United States Patent
Torres Rivera et al.

(10) Patent No.: US 10,799,434 B2
(45) Date of Patent: *Oct. 13, 2020

(54) CONCENTRATED SHAMPOO DOSAGE OF FOAM FOR PROVIDING HAIR CARE BENEFITS

(71) Applicant: The Procter & Gamble Company, Cincinnati, OH (US)

(72) Inventors: Jazmin Veronica Torres Rivera, Liberty Township, OH (US); Eric Scott Johnson, Hamilton, OH (US); Sarah Elizabeth Mullen, Cincinnati, OH (US); Sean Michael Renock, Loveland, OH (US); Todd Ryan Thompson, Loveland, OH (US); Jean Jianqun Zhao, Cincinnati, OH (US); Robert Wayne Glenn, Jr., Liberty Township, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 39 days.

This patent is subject to a terminal disclaimer.

(21) Appl. No.: 16/248,900

(22) Filed: Jan. 16, 2019

(65) Prior Publication Data

US 2019/0142711 A1 May 16, 2019

Related U.S. Application Data

(63) Continuation of application No. 15/788,938, filed on Oct. 20, 2017, now abandoned.

(60) Provisional application No. 62/411,218, filed on Oct. 21, 2016.

(51) Int. Cl.
| | | |
|---|---|---|
| *A61K 8/04* | (2006.01) | |
| *A61K 8/49* | (2006.01) | |
| *A61K 8/27* | (2006.01) | |
| *A61Q 5/02* | (2006.01) | |
| *A61K 8/31* | (2006.01) | |
| *A61Q 5/00* | (2006.01) | |
| *A61K 8/58* | (2006.01) | |
| *A61K 8/69* | (2006.01) | |

(52) U.S. Cl.
CPC ............. *A61K 8/046* (2013.01); *A61K 8/27* (2013.01); *A61K 8/31* (2013.01); *A61K 8/4926* (2013.01); *A61K 8/4933* (2013.01); *A61K 8/58* (2013.01); *A61K 8/69* (2013.01); *A61Q 5/006* (2013.01); *A61Q 5/02* (2013.01); *A61K 2800/58* (2013.01)

(58) Field of Classification Search
CPC ........ A61K 8/4933; A61K 8/046; A61K 8/31; A61K 8/69; A61K 8/58; A61Q 5/02; A61Q 5/006
See application file for complete search history.

(56) References Cited

U.S. PATENT DOCUMENTS

| | | | |
|---|---|---|---|
| 2,879,231 A | 3/1959 | Marshall | |
| 3,709,437 A * | 1/1973 | Wright | .............. B05B 7/0037 239/343 |
| 3,950,532 A | 4/1976 | Bouillon et al. | |
| 3,959,160 A | 5/1976 | Horsler et al. | |
| 4,309,119 A | 1/1982 | Wittersheim | |
| 4,329,334 A | 5/1982 | Su et al. | |
| 4,726,945 A | 2/1988 | Patel | |
| 4,839,166 A | 6/1989 | Grollier et al. | |
| 4,867,971 A | 9/1989 | Ryan et al. | |
| 4,997,641 A | 3/1991 | Hartnett | |
| 5,294,644 A | 3/1994 | Login et al. | |
| 5,332,569 A | 7/1994 | Wood et al. | |
| 5,364,031 A * | 11/1994 | Taniguchi | ............. B05B 7/0062 239/330 |
| 5,374,421 A | 12/1994 | Tashiro | |
| 5,417,965 A | 5/1995 | Janchitraponvej et al. | |
| 5,439,682 A | 8/1995 | Wivell | |
| 5,560,918 A | 10/1996 | Wivell | |
| 5,578,298 A | 11/1996 | Berthiaume | |
| 5,599,549 A | 2/1997 | Wivell | |
| 5,635,469 A | 6/1997 | Fowler et al. | |
| 5,747,436 A | 5/1998 | Patel et al. | |
| 5,776,444 A | 7/1998 | Birtwistle et al. | |
| 5,816,446 A | 10/1998 | Steindorf et al. | |
| 5,830,440 A | 11/1998 | Sturla et al. | |

(Continued)

FOREIGN PATENT DOCUMENTS

| | | |
|---|---|---|
| CA | 2078375 A1 | 3/1994 |
| CN | 102697668 B | 8/2013 |
| CN | 102697670 B | 7/2014 |
| CN | 102851015 B | 12/2014 |
| CN | 105769617 A | 7/2016 |
| DE | 4315396 A1 | 11/1994 |
| DE | 202005009618 U1 | 9/2005 |
| EP | 0574086 A2 | 12/1993 |
| EP | 1340485 A2 | 2/2003 |
| EP | 1346720 A2 | 9/2003 |
| EP | 1714678 A1 | 10/2006 |
| EP | 2042216 B1 | 9/2015 |
| JP | 58113300 | 7/1983 |
| JP | 58113300 A | 7/1983 |

(Continued)

OTHER PUBLICATIONS

Christensen et al., "Experimental Determination of Bubble Size Distribution in a Water Column by Interferometric Particle Imaging and Telecentric Direct Image Method", Student Report, Aalborg University, Jun. 3, 2014. (Year: 2014).*

(Continued)

*Primary Examiner* — Jianfeng Song
(74) *Attorney, Agent, or Firm* — Alexandra S. Anoff

(57) ABSTRACT

Described herein is a dosage of foam including from about 5 cm³ to about 70 cm³ of the foam. The foam includes from about 0.5 g to about 4 g of a detersive surfactant; from about 0.001 g to about 4 g propellant; a foam density of from about 0.10 g/cm³ to about 0.35 g/cm³; a bubble size distribution having an $R_{32}$ of from about 5 μm to about 100 μm; and a yield point of from about 5 Pa to about 100 Pa.

18 Claims, No Drawings

(56) References Cited

U.S. PATENT DOCUMENTS

| | | |
|---|---|---|
| 5,853,618 A | 12/1998 | Barker |
| 5,902,225 A | 5/1999 | Monson |
| 5,980,877 A | 11/1999 | Baravetto |
| 6,015,780 A | 1/2000 | Llosas Bigorra et al. |
| 6,020,303 A | 2/2000 | Cripe et al. |
| 6,039,933 A | 3/2000 | Samain et al. |
| 6,046,152 A | 4/2000 | Vinson et al. |
| 6,060,443 A | 5/2000 | Cripe et al. |
| 6,087,309 A | 7/2000 | Vinson et al. |
| 6,110,451 A | 8/2000 | Matz et al. |
| 6,133,222 A | 10/2000 | Vinson et al. |
| 6,153,569 A | 11/2000 | Halloran |
| 6,162,834 A | 12/2000 | Sebillotte-Arnaud et al. |
| 6,231,844 B1 | 5/2001 | Nambu |
| 6,268,431 B1 | 7/2001 | Snyder et al. |
| 6,284,225 B1 | 9/2001 | Bhatt |
| 6,329,331 B1 | 12/2001 | Aronson et al. |
| 6,335,312 B1 | 1/2002 | Coffindaffer et al. |
| 6,423,305 B1 | 7/2002 | Cauwet-Martin et al. |
| 6,451,300 B1 | 9/2002 | Dunlop et al. |
| 6,511,669 B1 | 1/2003 | Garnier et al. |
| 6,579,907 B1 | 6/2003 | Sebillotte-Arnaud et al. |
| 6,627,585 B1 | 9/2003 | Steer |
| 6,642,194 B2 | 11/2003 | Harrison |
| 6,649,155 B1 | 11/2003 | Dunlop et al. |
| 6,743,760 B1 | 6/2004 | Hardy et al. |
| 6,827,795 B1 | 12/2004 | Kasturi et al. |
| 6,897,253 B2 | 5/2005 | Schmucker-castner |
| 6,992,054 B2 | 1/2006 | Lee et al. |
| 7,217,752 B2 | 5/2007 | Schmucker-Castner et al. |
| 7,220,408 B2 | 5/2007 | Decoster et al. |
| 7,223,385 B2 | 5/2007 | Gawtrey et al. |
| 7,485,289 B2 | 2/2009 | Gawtrey et al. |
| 7,504,094 B2 | 3/2009 | Decoster et al. |
| 7,531,497 B2 | 5/2009 | Midha et al. |
| 7,541,320 B2 | 6/2009 | Dabkowski et al. |
| 7,659,233 B2 | 2/2010 | Hurley et al. |
| 7,666,825 B2 | 2/2010 | Wagner et al. |
| 7,820,609 B2 | 10/2010 | Soffin et al. |
| 7,829,514 B2 | 11/2010 | Paul et al. |
| 7,928,053 B2 | 4/2011 | Hecht et al. |
| 7,977,288 B2 | 7/2011 | SenGupta |
| 8,084,407 B2 | 12/2011 | Soffin et al. |
| 8,088,721 B2 | 1/2012 | Soffin et al. |
| 8,119,168 B2 | 2/2012 | Johnson |
| 8,124,063 B2 | 2/2012 | Harichian et al. |
| 8,300,949 B2 | 10/2012 | Xu |
| 8,388,699 B2 | 3/2013 | Wood |
| 8,401,304 B2 | 3/2013 | Cavallaro et al. |
| 8,435,501 B2 | 5/2013 | Peffly et al. |
| 8,437,556 B1 | 5/2013 | Saisan |
| 8,580,725 B2 | 11/2013 | Kuhlman et al. |
| 8,609,600 B2 | 12/2013 | Warr et al. |
| 8,653,014 B2 | 2/2014 | Hilvert |
| 8,675,919 B2 | 3/2014 | Maladen |
| 8,680,035 B2 | 3/2014 | Kuhlman et al. |
| 8,699,751 B2 | 4/2014 | Maladen |
| 8,709,385 B2 | 4/2014 | Tamarkin |
| 8,741,363 B2 | 6/2014 | Albrecht et al. |
| 8,771,765 B1 | 7/2014 | Fernandez |
| 8,795,635 B2 | 8/2014 | Tamarkin et al. |
| 9,006,162 B1 | 4/2015 | Rizk |
| 9,186,642 B2 | 11/2015 | Dihora et al. |
| 9,265,727 B1 | 2/2016 | Lowenborg |
| 9,296,550 B2 | 3/2016 | Smith |
| 9,308,398 B2 | 4/2016 | Hutton et al. |
| 9,428,616 B2 | 8/2016 | Wagner |
| 9,512,275 B2 | 12/2016 | Wagner |
| 9,610,239 B2 | 4/2017 | Feng |
| 9,682,021 B2 | 6/2017 | Tamarkin et al. |
| 9,949,901 B2 | 4/2018 | Zhao et al. |
| 9,968,535 B2 | 5/2018 | Kitko |
| 9,993,420 B2 | 6/2018 | Glenn, Jr. et al. |
| 10,311,575 B2 | 6/2019 | Stofel |
| 10,426,713 B2 | 10/2019 | Song |
| 10,441,519 B2 | 10/2019 | Zhao |
| 10,653,590 B2 | 5/2020 | Torres Rivera |
| 2001/0000467 A1 | 4/2001 | Murray |
| 2001/0006088 A1 | 7/2001 | Lyle |
| 2001/0006621 A1 | 7/2001 | Coupe et al. |
| 2001/0016565 A1 | 8/2001 | Bodet et al. |
| 2002/0028182 A1 | 3/2002 | Dawson |
| 2002/0037299 A1 | 3/2002 | Turowski-Wanke et al. |
| 2002/0172648 A1 | 11/2002 | Hehner et al. |
| 2002/0193265 A1 | 12/2002 | Perron et al. |
| 2002/0197213 A1 | 12/2002 | Schmenger et al. |
| 2003/0022799 A1 | 1/2003 | Alvarado et al. |
| 2003/0049292 A1 | 3/2003 | Turowski-Wanke et al. |
| 2003/0050150 A1 | 3/2003 | Tanaka |
| 2003/0059377 A1 | 3/2003 | Riley |
| 2003/0083210 A1 | 5/2003 | Goldberg |
| 2003/0108501 A1 | 6/2003 | Hofrichter |
| 2003/0147842 A1 | 8/2003 | Restle et al. |
| 2003/0154561 A1 | 8/2003 | Patel |
| 2003/0161802 A1 | 8/2003 | Flammer |
| 2003/0180246 A1 | 9/2003 | Frantz et al. |
| 2003/0185867 A1 | 10/2003 | Kerschner et al. |
| 2003/0223951 A1 | 12/2003 | Geary et al. |
| 2003/0228272 A1 | 12/2003 | Amjad et al. |
| 2004/0014879 A1 | 1/2004 | Denzer et al. |
| 2004/0144863 A1 | 7/2004 | Kendrick |
| 2004/0235689 A1 | 11/2004 | Sakai et al. |
| 2005/0020468 A1 | 1/2005 | Frantz et al. |
| 2005/0136011 A1 | 6/2005 | Nekludoff |
| 2005/0152863 A1 | 7/2005 | Brautigam |
| 2005/0233929 A1 | 10/2005 | Queen |
| 2006/0002880 A1 | 1/2006 | Peffly |
| 2006/0057075 A1 | 3/2006 | Arkin et al. |
| 2006/0057097 A1 | 3/2006 | Derici |
| 2006/0079417 A1 | 4/2006 | Wagner |
| 2006/0079418 A1 | 4/2006 | Wagner et al. |
| 2006/0079419 A1 | 4/2006 | Wagner et al. |
| 2006/0079420 A1 | 4/2006 | Wagner et al. |
| 2006/0079421 A1 | 4/2006 | Wagner et al. |
| 2006/0090777 A1 | 5/2006 | Hecht et al. |
| 2006/0110415 A1 | 5/2006 | Gupta |
| 2006/0120982 A1 | 6/2006 | Derici et al. |
| 2006/0120988 A1 | 6/2006 | Bailey et al. |
| 2006/0183662 A1 | 8/2006 | Crotty et al. |
| 2006/0210139 A1 | 9/2006 | Carroll |
| 2006/0276357 A1 | 12/2006 | Smith, III et al. |
| 2007/0072781 A1 | 3/2007 | Soffin et al. |
| 2007/0110700 A1 | 5/2007 | Wells |
| 2007/0154402 A1 | 7/2007 | Trumbore et al. |
| 2007/0155637 A1 | 7/2007 | Smith, III et al. |
| 2007/0160555 A1 | 7/2007 | Staudigel |
| 2007/0179207 A1 | 8/2007 | Fernandez de Castro et al. |
| 2007/0269397 A1 | 11/2007 | Terada |
| 2007/0292380 A1 | 12/2007 | Staudigel |
| 2008/0008668 A1 | 1/2008 | Harichian et al. |
| 2008/0019928 A1 | 1/2008 | Franzke |
| 2008/0063618 A1 | 3/2008 | Johnson |
| 2008/0138442 A1 | 6/2008 | Johnson |
| 2008/0152610 A1 | 6/2008 | Cajan |
| 2008/0206179 A1 | 8/2008 | Peffly |
| 2008/0260655 A1 | 10/2008 | Tamarkin et al. |
| 2008/0261844 A1* | 10/2008 | Ruppert ............... A61Q 19/10 510/158 |
| 2008/0317698 A1 | 12/2008 | Wells et al. |
| 2009/0029900 A1 | 1/2009 | Cetti et al. |
| 2009/0041702 A1 | 2/2009 | Molenda |
| 2009/0062406 A1 | 3/2009 | Loeffler |
| 2009/0155383 A1 | 6/2009 | Kitko et al. |
| 2009/0178210 A1 | 7/2009 | Bistram |
| 2009/0197784 A1 | 8/2009 | Ainger |
| 2009/0221463 A1 | 9/2009 | Kitko et al. |
| 2009/0312224 A1 | 12/2009 | Yang et al. |
| 2010/0183539 A1 | 7/2010 | Bernhardt |
| 2010/0310644 A1 | 12/2010 | Liebmann |
| 2011/0008267 A1 | 1/2011 | Arkin et al. |
| 2011/0165107 A1 | 7/2011 | Derks et al. |
| 2011/0171155 A1 | 7/2011 | Federle |
| 2011/0232668 A1 | 9/2011 | Hoffmann et al. |
| 2011/0269657 A1 | 11/2011 | Dihora et al. |

(56) References Cited

U.S. PATENT DOCUMENTS

| | | |
|---|---|---|
| 2011/0319790 A1 | 12/2011 | Kost et al. |
| 2012/0031419 A1 | 2/2012 | Batt |
| 2012/0034173 A1 | 2/2012 | Batt |
| 2012/0100091 A1 | 4/2012 | Hata et al. |
| 2012/0100092 A1 | 4/2012 | Murray |
| 2012/0291911 A1 | 11/2012 | Smith |
| 2012/0316095 A1 | 12/2012 | Wei et al. |
| 2013/0053295 A1 | 2/2013 | Kinoshita et al. |
| 2013/0053300 A1 | 2/2013 | Scheibel et al. |
| 2013/0089587 A1 | 4/2013 | Staudigel |
| 2013/0115173 A1 | 5/2013 | Trumbore et al. |
| 2013/0143784 A1 | 6/2013 | Rizk |
| 2013/0150338 A1 | 6/2013 | Ananthapadmanabhan |
| 2013/0156712 A1 | 6/2013 | Frantz |
| 2013/0189212 A1 | 7/2013 | Jawale et al. |
| 2013/0243718 A1 | 9/2013 | Pasquet |
| 2013/0280192 A1 | 10/2013 | Carter et al. |
| 2013/0280202 A1 | 10/2013 | Stella et al. |
| 2013/0284195 A1 | 10/2013 | Murdock |
| 2013/0296289 A1 | 11/2013 | Hall et al. |
| 2014/0037703 A1 | 2/2014 | Dihora et al. |
| 2014/0039066 A1 | 2/2014 | Grimadell et al. |
| 2014/0131395 A1 | 5/2014 | Chang |
| 2014/0171471 A1* | 6/2014 | Krueger .................. A61K 8/97 |
| | | 514/345 |
| 2014/0216495 A1* | 8/2014 | Bureiko ................. A45D 19/00 |
| | | 132/317 |
| 2014/0228268 A1 | 8/2014 | Fahl et al. |
| 2014/0237732 A1 | 8/2014 | Zuedel Fernandes et al. |
| 2014/0309154 A1 | 10/2014 | Carter et al. |
| 2014/0335041 A1 | 11/2014 | Peffly et al. |
| 2014/0348884 A1 | 11/2014 | Hilvert et al. |
| 2014/0348886 A1 | 11/2014 | Johnson et al. |
| 2015/0021496 A1 | 1/2015 | Shabbir |
| 2015/0098921 A1 | 4/2015 | Franzke et al. |
| 2015/0218496 A1 | 8/2015 | Schmiedel et al. |
| 2015/0297489 A1* | 10/2015 | Kleinen .................. C11D 1/94 |
| | | 514/785 |
| 2015/0359725 A1 | 12/2015 | Glenn, Jr. et al. |
| 2016/0008257 A1 | 1/2016 | Zhou et al. |
| 2016/0113849 A1 | 4/2016 | Grimadell et al. |
| 2016/0193125 A1 | 7/2016 | Jones et al. |
| 2016/0279048 A1 | 9/2016 | Jayaswal et al. |
| 2016/0303043 A1 | 10/2016 | Khoury |
| 2016/0309871 A1 | 10/2016 | Torres Rivera et al. |
| 2016/0310369 A1 | 10/2016 | Thompson et al. |
| 2016/0310370 A1 | 10/2016 | Zhao et al. |
| 2016/0310386 A1 | 10/2016 | Smith, III et al. |
| 2016/0310388 A1 | 10/2016 | Smith, III et al. |
| 2016/0310389 A1 | 10/2016 | Thompson et al. |
| 2016/0310390 A1 | 10/2016 | Smith, III et al. |
| 2016/0310391 A1 | 10/2016 | Smith, III et al. |
| 2016/0310393 A1 | 10/2016 | Chang et al. |
| 2016/0310402 A1 | 10/2016 | Zhao et al. |
| 2016/0354300 A1 | 12/2016 | Thompson et al. |
| 2017/0165164 A1 | 6/2017 | Zhao et al. |
| 2017/0165165 A1 | 6/2017 | Zhao et al. |
| 2017/0209359 A1 | 7/2017 | Zhao et al. |
| 2017/0252273 A1 | 9/2017 | Renock et al. |
| 2017/0278249 A1 | 9/2017 | Stofel et al. |
| 2017/0304172 A1 | 10/2017 | Chang et al. |
| 2017/0304185 A1 | 10/2017 | Glenn, Jr. et al. |
| 2018/0057451 A1 | 3/2018 | Owens et al. |
| 2018/0110688 A1 | 4/2018 | Torres Rivera et al. |
| 2018/0110689 A1 | 4/2018 | Torres Rivera et al. |
| 2018/0110690 A1 | 4/2018 | Torres Rivera et al. |
| 2018/0110691 A1 | 4/2018 | Torres Rivera et al. |
| 2018/0110692 A1 | 4/2018 | Torres Rivera et al. |
| 2018/0110693 A1 | 4/2018 | Renock et al. |
| 2018/0110694 A1 | 4/2018 | Renock et al. |
| 2018/0110695 A1 | 4/2018 | Thompson et al. |
| 2018/0110696 A1 | 4/2018 | Johnson et al. |
| 2018/0110704 A1 | 4/2018 | Zhao et al. |
| 2018/0110707 A1 | 4/2018 | Zhao et al. |
| 2018/0110710 A1 | 4/2018 | Zhao et al. |
| 2018/0110714 A1 | 4/2018 | Glenn, Jr. et al. |
| 2018/0116937 A1 | 5/2018 | Park et al. |
| 2018/0116941 A1 | 5/2018 | Wang |
| 2018/0221266 A1 | 8/2018 | Zhao et al. |
| 2018/0344613 A1 | 12/2018 | Zhao et al. |
| 2018/0344614 A1 | 12/2018 | Zhao et al. |
| 2019/0105242 A1 | 4/2019 | Song |
| 2019/0105243 A1 | 4/2019 | Song |
| 2019/0105244 A1 | 4/2019 | Song |
| 2019/0105245 A1 | 4/2019 | Song |
| 2019/0105246 A1 | 4/2019 | Cochran |
| 2019/0105247 A1 | 4/2019 | Song |
| 2019/0117543 A1 | 4/2019 | Zhao |
| 2019/0117544 A1 | 4/2019 | Zhao |
| 2019/0117545 A1 | 4/2019 | Zhao |
| 2019/0183777 A1 | 6/2019 | Gillis |
| 2019/0183778 A1 | 6/2019 | Glenn, Jr. |
| 2019/0192405 A1 | 6/2019 | Zhao |
| 2019/0240121 A1 | 8/2019 | Torres Rivera |
| 2019/0307298 A1 | 10/2019 | Zhao |
| 2020/0000690 A1 | 1/2020 | Renock |
| 2020/0129402 A1 | 4/2020 | Jamadagni |
| 2020/0163846 A1 | 5/2020 | Song |
| 2020/0237628 A1 | 7/2020 | Torres Rivera |

FOREIGN PATENT DOCUMENTS

| | | |
|---|---|---|
| JP | H08310924 A | 11/1996 |
| JP | 2964226 B2 | 10/1999 |
| JP | 3069802 B2 | 7/2000 |
| JP | 2002226889 A | 8/2002 |
| JP | 3634988 B2 | 3/2005 |
| JP | 3634991 B2 | 3/2005 |
| JP | 3634996 B2 | 3/2005 |
| JP | 2005187359 A | 7/2005 |
| JP | 2008214292 A | 9/2008 |
| JP | 5041113 B2 | 7/2012 |
| JP | 6046394 B2 | 1/2014 |
| JP | 5667790 B2 | 2/2015 |
| KR | 1020080111280 | 12/2008 |
| KR | 20140060882 A | 5/2014 |
| WO | 199325650 A1 | 12/1993 |
| WO | WO9502389 A1 | 1/1995 |
| WO | WO9726854 A1 | 7/1997 |
| WO | WO9823258 A1 | 6/1998 |
| WO | WO9918928 A1 | 4/1999 |
| WO | 9924004 A1 | 5/1999 |
| WO | 0012553 A1 | 3/2000 |
| WO | WO0142409 A1 | 6/2001 |
| WO | 0148021 A1 | 7/2001 |
| WO | WO2005023975 A1 | 3/2005 |
| WO | WO2009016555 A1 | 2/2009 |
| WO | 2009053931 A2 | 4/2009 |
| WO | WO2010052147 A2 | 5/2010 |
| WO | WO2012055587 A1 | 5/2012 |
| WO | WO2012084970 A1 | 6/2012 |
| WO | WO2013010706 A1 | 1/2013 |
| WO | WO2014148245 A1 | 9/2014 |
| WO | 2016147196 A1 | 9/2016 |
| WO | 2017052161 A1 | 3/2017 |
| WO | 2017140798 A1 | 8/2017 |
| WO | 2017207685 A1 | 12/2017 |
| WO | 2018023180 A1 | 2/2018 |

OTHER PUBLICATIONS

"Soda Shampoo", Mintel Database, Apr. 2015.
"Treatment Foam for Recurrent Scaling Conditions", Mintel Database, Aug. 2007.
All Final and Non-Final Office Actions for U.S. Appl. No. 16/156,045.
All Final and Non-Final Office Actions for U.S. Appl. No. 15/135,657.
All Final and Non-Final Office Actions for U.S. Appl. No. 15/135,663.
All Final and Non-Final Office Actions for U.S. Appl. No. 15/135,677.
All Final and Non-Final Office Actions for U.S. Appl. No. 15/135,701.
All Final and Non-Final Office Actions for U.S. Appl. No. 15/135,998.
All Final and Non-Final Office Actions for U.S. Appl. No. 15/145,696.
All Final and Non-Final Office Actions for U.S. Appl. No. 15/2788,938.

(56) References Cited

OTHER PUBLICATIONS

All Final and Non-Final Office Actions for U.S. Appl. No. 15/299,860.
All final and non-final office actions for U.S. Appl. No. 15/379,660.
All final and non-final office actions for U.S. Appl. No. 15/379,674.
All final and non-final office actions for U.S. Appl. No. 15/448,911.
All final and non-final office actions for U.S. Appl. No. 15/467,317.
All Final and Non-Final Office Actions for U.S. Appl. No. 15/481,777.
All Final and Non-Final Office Actions for U.S. Appl. No. 15/788,895.
All Final and Non-Final Office Actions for U.S. Appl. No. 15/788,949.
All Final and Non-Final Office Actions for U.S. Appl. No. 15/788,998.
All Final and Non-Final Office Actions for U.S. Appl. No. 15/789,010.
All Final and Non-Final Office Actions for U.S. Appl. No. 15/789,020.
All Final and Non-Final Office Actions for U.S. Appl. No. 15/789,030.
All Final and Non-Final Office Actions for U.S. Appl. No. 15/789,038.
All Final and Non-Final Office Actions for U.S. Appl. No. 15/789,044.
All Final and Non-Final Office Actions for U.S. Appl. No. 15/789,081.
All Final and Non-Final Office Actions for U.S. Appl. No. 15/789,172.
All Final and Non-Final Office Actions for U.S. Appl. No. 15/789,188.
All Final and Non-Final Office Actions for U.S. Appl. No. 15/789,208.
All Final and Non-final Office Actions for U.S. Appl. No. 15/923,499.
All final and non-final office actions for U.S. Appl. No. 15/962,327.
All final and non-final office actions for U.S. Appl. No. 15/962,351.
All final and non-final office actions for U.S. Appl. No. 16/001,045.
All final and non-final office actions for U.S. Appl. No. 16/001,053.
All final and non-final office actions for U.S. Appl. No. 16/001,058.
All final and non-final office actions for U.S. Appl. No. 16/001,064.
All Final and Non-Final Office Actions for U.S. Appl. No. 16/156,015.
All Final and Non-Final Office Actions for U.S. Appl. No. 16/156,038.
All Final and Non-Final Office Actions for U.S. Appl. No. 16/156,053.
All Final and Non-Final Office Actions for U.S. Appl. No. 16/156,066.
All Final and Non-Final Office Actions for U.S. Appl. No. 16/156,072.
All final and non-final office actions for U.S. Appl. No. 16/165,016.
All final and non-final office actions for U.S. Appl. No. 16/165,033.
All final and non-final office actions for U.S. Appl. No. 16/165,044.
All final and non-final office actions for U.S. Appl. No. 16/170,498.
All final and non-final office actions for U.S. Appl. No. 16/170,516.
All final and non-final office actions for U.S. Appl. No. 16/170,711.
Dehyquart Guar: Published Nov. 2010.
PCT International Search Report and Written Opinion for PCT/US2016/028728 dated Aug. 5, 2016.
PCT International Search Report and Written Opinion for PCT/US2016/028729 dated Jun. 15, 2016.
PCT International Search Report and Written Opinion for PCT/US2016/028730 dated Aug. 5, 2016.
PCT International Search Report and Written Opinion for PCT/US2016/028735 dated Jul. 25, 2016.
PCT International Search Report and Written Opinion for PCT/US2016/028736 dated Jul. 25, 2016.
PCT International Search Report and Written Opinion for PCT/US2016/028742 dated Jul. 18, 2016.
PCT International Search Report and Written Opinion for PCT/US2016/058123 dated Dec. 21, 2016.
PCT International Search Report and Written Opinion for PCT/US2016/066752 dated Feb. 22, 2017.
PCT International Search Report and Written Opinion for PCT/US2016/066757 dated Feb. 22, 2017.
PCT International Search Report and Written Opinion for PCT/US2017/020604 dated May 11, 2017.
PCT International Search Report and Written Opinion for PCT/US2017/022737 dated Jun. 22, 2017.
PCT International Search Report and Written Opinion for PCT/US2017/057486 dated Jan. 9, 2018.
PCT International Search Report and Written Opinion for PCT/US2017/057487 dated Dec. 19, 2017.
PCT International Search Report and Written Opinion for PCT/US2017/057488 dated Dec. 12, 2017.
PCT International Search Report and Written Opinion for PCT/US2017/057497 dated Jan. 8, 2018.
PCT International Search Report and Written Opinion for PCT/US2017/057503 dated Dec. 13, 2017.
PCT International Search Report and Written Opinion for PCT/US2017/057507 dated Dec. 13, 2017.
PCT International Search Report and Written Opinion for PCT/US2017/057510 dated Jan. 11, 2018.
PCT International Search Report and Written Opinion for PCT/US2017/057511 dated Feb. 2, 2018.
PCT International Search Report and Written Opinion for PCT/US2017/057514 dated Jan. 10, 2018.
PCT International Search Report and Written Opinion for PCT/US2017/057515 dated Dec. 11, 2017.
PCT International Search Report and Written Opinion for PCT/US2017/057522 dated Feb. 2, 2018.
PCT International Search Report and Written Opinion for PCT/US2017/057533 dated Jan. 8, 2018.
PCT International Search Report and Written Opinion for PCT/US2017/057541 dated Dec. 22, 2017.
PCT International Search Report and Written Opinion for PCT/US2018/029313 dated Jul. 11, 2018.
PCT International Search Report and Written Opinion for PCT/US2018/029315 dated Jun. 27, 2018.
PCT International Search Report and Written Opinion for PCT/US2018/036181 dated Aug. 3, 2018.
PCT International Search Report and Written Opinion for PCT/US2018/036185 dated Aug. 3, 2018.
Practical Modern Hair Science, Published 2012.
"Deep Image Matting", Ning Xu et al, Beckman Institute for Advanced Science and Technology, University of Illinois at Urbana-Champaign, Adobe Research, Mar. 10, 2017.
"Natural Detangling Shampoo", Mintel Database, Sep. 13, 2017.
All final and non-final office actions for U.S. Appl. No. 16/226,914.
All final and non-final office actions for U.S. Appl. No. 16/226,927.
All final and non-final office actions for U.S. Appl. No. 16/285,535.
All final and non-final office actions for U.S. Appl. No. 16/376,033.
All final and non-final office actions for U.S. Appl. No. 16/390,270.
All final and non-final office actions for U.S. Appl. No. 16/532,556.
All final and non-final office actions for U.S. Appl. No. 16/846,594.
Anonymous: "MERQUAT Polyquaternium 47 Series, Water Soluble Polymers for Personal Care", Jul. 30, 2017, URL: https://www.in-cosmetics.com/_novadocuments/2729, retrieved on Dec. 21, 2018.
Carbopol Aqua SF-1 Polymer Technical Data Sheet, TDS-294, Dec. 2000.
Christensen et al., "Experimental Determination of Bubble Size Distribution in a Water Column by Interferometric Particle Imaging and Telecentric Direct Image Method", Student Report, Aalborg University, Jun. 3, 2014.
D'Souza et al., Shampoo and Conditioners: What a Dermatologist Should Know? Indian J Dermatol, May-Jun. 2015 60(3), 248-254 (2015).
Hair Care/Conditioning Polymers Differentiation, Anonymous, Feb. 1, 2017, URL: http://www.biochim.it./assets/site/media/allegati/cosmetica/hair-care/tab-merquat-hair-care.pdf, retrieved on Dec. 20, 2018, p. 1.
Inspection certificate for Hostapon® CCG, Clariant Ibérica Producción, S.A., May 6, 2019.
Musazzi, "Emulsion versus nonoemulsion: how much is the formulative shift critical for a cosmetic product?" (Drug Deliv. and Trans. Res. (2018) 8:414-421 (Year: 2018).
PCT International Search Report and Written Opinion for PCT/US2018/055102 dated Jan. 9, 2019.
PCT International Search Report and Written Opinion for PCT/US2018/055103 dated Jan. 9, 2019.
PCT International Search Report and Written Opinion for PCT/US2018/055104 dated Jan. 18, 2019.
PCT International Search Report and Written Opinion for PCT/US2018/055105 dated Jan. 8, 2019.
PCT International Search Report and Written Opinion for PCT/US2018/055106 dated Jan. 16, 2019.
PCT International Search Report and Written Opinion for PCT/US2018/055107 dated Jan. 28, 2019.
PCT International Search Report and Written Opinion for PCT/US2018/056669 dated Jan. 31, 2019.
PCT International Search Report and Written Opinion for PCT/US2018/056673 dated Feb. 5, 2019.

(56) References Cited

OTHER PUBLICATIONS

PCT International Search Report and Written Opinion for PCT/US2018/056674 dated Feb. 5, 2019.
PCT International Search Report and Written Opinion for PCT/US2018/057451 dated Feb. 25, 2019.
PCT International Search Report and Written Opinion for PCT/US2018/057476 dated Jan. 18, 2019.
PCT International Search Report and Written Opinion for PCT/US2018/066697 dated Mar. 15, 2019.
PCT International Search Report and Written Opinion for PCT/US2018/066701 dated Mar. 15, 2019.
PCT International Search Report and Written Opinion for PCT/US2019/025923 dated Jun. 24, 2019.
PCT International Search Report and Written Opinion for PCT/US2019/057974 dated Feb. 3, 2020.
Polyquaternium: "Final Report on the Safety Assessment of the Polyquaternium-10", Journal of the American College of Toxicology, Jan. 1, 1988, URL: http://www.beauty-review.nl/wp-content/uploads/2015/02/Final-Report-on-the Safety-Assessment-of-Polyquaternium-10.pdf, retrieved on Dec. 20, 2018.
Product Bulletin, Amphosol® CG, Cocamidopropyl Betaine, Stepan Company, Jun. 2011.
Product Data Sheet for Chemoryl™ LS Surfactant, Sodium Lauroyl Sarcosinate, Lubrizol Advanced Materials, Inc., Mar. 24, 2020.
Product Data Sheet, Eversoft™ UCS-40S, Disodium Cocoyl Glutamate (Sodium Cocoyl Glutamate*), Sino Lion USA, Jul. 2018.
Product Fact Sheet—Hostapon® CCG, mild anionic surfactant for the cosmetic industry, Clariant International Ltd., Aug. 2014.
Product Fact Sheet, Hostapon® CGN, Mild anionic surfactant for the cosmetic industry, Clariant International Ltd., Jan. 2016.
S. Herrwerth et al.: "Highly Concentrated Cocamidopropyl Betaine—The Latest Developments for Improved Sustainability and Enhanced Skin Care", Tenside, Surfactants, Detergents, vol. 45, No. 6, Nov. 1, 2008, pp. 304-308, p. 305—left-hand column.
Schaefer, Katie, "Eco-friendly, Non-flammable Liquified Gas Propellant", https://www.cosmeticsandtoiletries.com/formulating/function/aids/138418589.html#close-olyticsmodal. Published Jan. 30, 2012.
UL Prospector® Product Data Sheet, Plantacare® 818 UP, C8-16 fatty alcohol glucoside, BASF, May 21, 2015.

* cited by examiner

CONCENTRATED SHAMPOO DOSAGE OF FOAM FOR PROVIDING HAIR CARE BENEFITS

FIELD OF THE INVENTION

Described herein is a concentrated shampoo dosage of foam which delivers hair care benefits.

BACKGROUND OF THE INVENTION

Foams for the hair care represent an attractive form to the consumers. A shampoo product delivered via foam is readily spread on hair and enables hair cleansing without leaving significant residue on hair. The low density of the foam necessitates a high surfactant composition in order for the consumer to receive the appropriate level of cleansing in a realistic product volume in one dose. The delivery of shampoo and conditioner products via foam is not common today. Thus, the appearance of the delivered form must be delightful to the consumer and impact the perception of the product benefit. Based on the foregoing, there is a need for concentrated shampoo products that are delivered as foams in a consumer preferred visual appearance and rheology profile.

Described herein are dosages of foam having specific yield point and density profiles which provide a high consumer acceptance rating in terms of hair conditioning benefits based on a visual examination of dosages of foam.

SUMMARY OF THE INVENTION

Described herein is a dosage of foam comprising from about 5 cm³ to about 150 cm³ of the foam wherein the foam comprises (a) from about 0.5 g to about 4 g of a detersive surfactant by weight of the foam; (b) from about 0.001 g to about 4 g propellant by weight of the foam; (c) a foam density of from about 0.10 g/cm³ to about 0.35 g/cm³; (d) a bubble size distribution comprising an $R_{32}$ of from about 5 µm to about 90 µm; and (e) a yield point of from about 10 Pa to about 100 Pa.

Also described herein is a dosage of foam comprising from about 5 cm³ to about 70 cm³ of the foam wherein the foam comprises (a) from about 0.5 g to about 4 g of a detersive surfactant by weight of the foam; (b) from about 0.00005 g to about 0.25 g of a cationic deposition polymer by weight of the foam; (c) a foam density of from about 0.10 g/cm³ to about 0.35 g/cm³; (d) a bubble size distribution comprising an $R_{32}$ of from about 5 µm to about 90 µm; (e) and a yield point of from about 10 Pa to about 100 Pa.

DETAILED DESCRIPTION OF THE INVENTION

While the specification concludes with claims particularly pointing out and distinctly claiming the invention, it is believed that the dosage of foam described herein will be better understood from the following description.

As used herein, the term "fluid" includes liquids and gels.

As used herein, the articles including "a" and "an" when used in a claim, are understood to mean one or more of what is claimed or described.

As used herein, "comprising" means that other steps and other ingredients which do not affect the end result can be added. This term encompasses the terms "consisting of" and "consisting essentially of".

As used herein, "mixtures" is meant to include a simple combination of materials and any compounds that may result from their combination.

As used herein, "molecular weight" or "Molecular weight" refers to the weight average molecular weight unless otherwise stated. Molecular weight of polymers may be measured using industry standard method, gel permeation chromatography ("GPC").

As used herein, the terms "include," "includes," and "including," are meant to be non-limiting and are understood to mean "comprise," "comprises," and "comprising," respectively.

As used herein, the term "viscosity reducing agent" can mean organic compounds having a molecular weight of from about 100 to about 300 daltons, alternatively from about 125 daltons to about 300 daltons. Additionally, the viscosity reducing agents may have a water solubility at between 23 and 25 degrees Celsius of from about 900 to 50,000 mg/L.

All percentages, parts and ratios are based upon the total weight of the compositions of the present invention, unless otherwise specified. All such weights as they pertain to listed ingredients are based on the active level and, therefore, do not include carriers or by-products that may be included in commercially available materials.

Unless otherwise noted, all component or composition levels are in reference to the active portion of that component or composition, and are exclusive of impurities, for example, residual solvents or by-products, which may be present in commercially available sources of such components or compositions.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Dosage of Foam

The dosage of foam can have a volume of from about 5 cm³ to about 70 cm³, alternatively from about 10 cm³ to about 70 cm³, alternatively from about 15 cm³ to about 70 cm³, alternatively from about 20 cm³ to about 70 cm³, alternatively from about 30 cm³ to about 70 cm³, alternatively from about 5 cm³ to about 40 cm³, alternatively from about 7.5 cm³ to about 30 cm³, alternatively from about 10 cm³ to about 90 cm³, alternatively from about 5 cm³ to about 150 cm³, alternatively from about 5 cm³ to about 30 cm³, alternatively from about 2.5 cm³ to about 40 cm³, alternatively from about 10 cm³ to about 50 cm³, alternatively from about 2.5 cm³ to about 40 cm³, alternatively from about 15 cm³ to about 90 cm³, alternatively from about 15 cm³ to about 150 cm³, alternatively from about 15 cm³ to about 30 cm³, alternatively from about 15 cm³ to about 40 cm³, alternatively from about 15 cm³ to about 50 cm³, alternatively from about 20 cm³ to about 60 cm³, alternatively from about 20 cm³ to about 50 cm³, and alternatively from about 15 cm³ to about 40 cm³.

The dosage of foam can comprise from about 0.5 g to about 12 g, alternatively from about 0.5 g to about 8 g, alternatively from about 0.5 g to about 4 g, alternatively from about 0.5 g to about 3 g, alternatively from about 0.5 g to about 1.75 g, alternatively from about 1 g to about 1.25 g, alternatively from about 1 g to about 8 g, alternatively from about 1.25 g to about 4 g, alternatively from about 1.5 g to about 3 g, alternatively from about 1.25 g to about 2.0 g, alternatively from about 1 g to about 1.75 g, alternatively from about 1 g to about 1.25 g of a detersive surfactant by weight of the foam.

The dosage of foam can also comprise from about 0.0001 g to about 5 g, alternatively from about 0.001 g to about 5 g, alternatively from about 0.001 g to about 4 g, alternatively from about 0.01 g to about 4 g, alternatively from about 0.05 g to about 3 g, alternatively from about 0.1 to about 2 g, alternatively from about 0.075 g to about 2 g propellant by weight of the foam, alternatively from about 0.05 g to about 1 g, and alternatively from about 0.05 g to about 0.5 g.

The dosage of foam can also have a foam density of from about 0.10 g/cm$^3$ to about 0.35 g/cm$^3$; alternatively from about 0.15 g/cm$^3$ to about 0.35 g/cm$^3$; and alternatively from about 0.20 g/cm$^3$ to about 0.35 g/cm$^3$.

The dosage of foam can also have a bubble size distribution comprising an $R_{32}$ of from about 5 μm to about 100 μm, alternatively from about 5 μm to 90 μm, alternatively from about 10 μm to about 60 μm, alternatively from about 20 μm to about 50 μm, and alternatively from about 25 μm to about 40 μm.

The dosage of foam can have a yield point of from about 5 Pa to about 100 Pa, alternatively about 10 Pa to about 100 Pa, alternatively from about 20 Pa to about 100 Pa, alternatively from about 25 Pa to about 100 Pa, and alternatively from about 38 Pa to about 100 Pa.

The dosage of foam can comprise from about 0.00005 g to about 0.25 g of a cationic deposition polymer by weight of the foam.

Hair Care Compositions

Also described herein are hair care compositions that can deliver the dosages of foam described herein when actuated via a mechanical or aerosol dispenser.

Detersive Surfactant

The hair care compositions described herein may comprise greater than about 20% by weight of a surfactant system which provides cleaning performance to the composition. The surfactant system comprises an anionic surfactant and/or a combination of anionic surfactants, with a co-surfactant selected from the group consisting of amphoteric, zwitterionic, nonionic and mixtures thereof. Various examples and descriptions of detersive surfactants are set forth in U.S. Pat. No. 8,440,605; U.S. Patent Application Publication No. 2009/155383; and U.S. Patent Application Publication No. 2009/0221463, which are incorporated herein by reference in their entirety.

The hair care composition may comprise from about 10% to about 40%, from about 15% to about 36%, from about 18% to about 32%, from about 20% to about 30%, and/or from about 22% to about 28% by weight of one or more anionic surfactants.

Anionic surfactants suitable for use herein include alkyl sulfates and alkyl ether sulfates of the formula ROSO$_3$M and RO(C$_2$H$_4$O)$_x$SO$_3$M, wherein R is alkyl or alkenyl of from about 8 to about 18 carbon atoms, x is 1 to 10, and M is a water-soluble cation such as ammonium, sodium, potassium, and triethanolamine cation or salts of the divalent magnesium ion with two anionic surfactant anions. The alkyl ether sulfates may be made as condensation products of ethylene oxide and monohydric alcohols having from about 8 to about 24 carbon atoms. The alcohols can be derived from fats such as coconut oil, palm oil, palm kernel oil, or tallow, or can be synthetic.

The composition of the present invention can also include anionic surfactants selected from the group consisting of:

a) R$_1$O(CH$_2$CHR$_3$O)$_y$SO$_3$M;

b) CH$_3$(CH$_2$)$_z$CHR$_2$CH$_2$O(CH$_2$CHR$_3$O)$_y$SO$_3$M; and c) mixtures thereof, where R$_1$ represents CH$_3$(CH$_2$)$_{10}$, R$_2$ represents H or a hydrocarbon radical comprising 1 to 4 carbon atoms such that the sum of the carbon atoms in z and R$_2$ is 8, R$_3$ is H or CH$_3$, y is 0 to 7, the average value of y is about 1 when y is not zero (0), and M is a monovalent or divalent, positively-charged cation.

Anionic surfactants suitable for use in the compositions are the alkyl and alkyl ether sulfates. Other suitable anionic surfactants are the water-soluble salts of organic, sulfuric acid reaction products. Still other suitable anionic surfactants are the reaction products of fatty acids esterified with isethionic acid and neutralized with sodium hydroxide. Other similar anionic surfactants are described in U.S. Pat. Nos. 2,486,921; 2,486,922; and 2,396,278, which are incorporated herein by reference in their entirety.

Examples of additional anionic surfactants suitable for use herein include, but are not limited to, ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, monoethanolamine cocoyl sulfate, sodium trideceth-1 sulfate, sulfate, sodium trideceth-2 sulfate, sulfate, sodium trideceth-3 sulfate, sodium tridecyl sulfate, sodium methyl lauroyl taurate, sodium undecyl sulfate, sodium decyl sulfate, sodium methyl cocoyl taurate, sodium lauroyl isethionate, sodium cocoyl isethionate, sodium laurethsulfosuccinate, sodium laurylsulfosuccinate, sodium tridecyl benzene sulfonate, sodium dodecyl benzene sulfonate, and mixtures thereof.

Some non-limiting examples of anionic surfactants are:
Alkyl Sulfates:

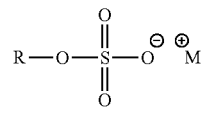

Alkyl sulfates where R is C$_8$-C$_{24}$ alkyl (linear or branched, saturated or unsaturated) or mixtures thereof and M$^+$ is monovalent cation. Examples include Sodium lauryl sulfate (where R is C$_{12}$ alkyl and M$^+$ is Na$^+$), ammonium lauryl sulfate (where R is C$_{12}$ alkyl and M$^+$ is NH$_3^+$), and sodium coco-sulfate (where R is coconut alkyl and M$^+$ is Na$^+$);

Alkyl Ether Sulfates:

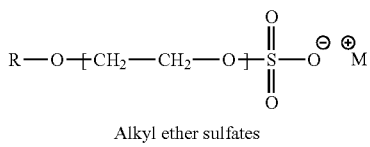

Alkyl ether sulfates where R is $C_8$-$C_{24}$ alkyl (linear or branched, saturated or unsaturated) or mixtures thereof, n=1-12, and $M^+$ is monovalent cation. Examples include sodium laureth sulfate (where R is $C_{12}$ alkyl and $M^+$ is $Na^+$, n=1-3), ammonium laureth sulfate (where R is $C_{12}$ alkyl, $M^+$ is $NH_3^+$, n=1-3), and Sodium trideceth sulfate (where R is $C_{13}$ alkyl, $M^+$ is $Na^+$, and n=1-4);

Alkyl Glyceryl Ether Sulfonates:

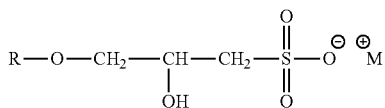

where $R=C_8$-$C_{24}$ alkyl (linear or branched, saturated or unsaturated) or mixtures thereof and $M^+$=monovalent cation, such as Sodium Cocoglyceryl Ether Sulfonate (R=coco alkyl, $M^+$=$Na^+$);

Alpha Olefin Sulfonates Prepared by Sulfonation of Long Chain Alpha Olefins. Alpha Olefin Sulfonates Consist of Mixtures of Alkene Sulfonates:

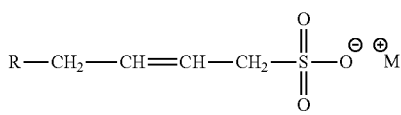

where $R=C_8$-$C_{18}$ alkyl or mixtures thereof and $M^+$=monovalent cation;

Hydroxyalkyl Sulfonates:

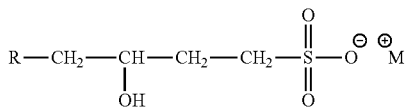

where $R=C_4$-$C_{18}$ alkyl or mixtures thereof and $M^+$=monovalent cation. Examples include Sodium C12-14 Olefin Sulfonate (R=C8-C10 alkyl, $M^+$=$Na^+$) and Sodium C 14-16 Olefin Sulfonate (R=$C_{10}$-$C_{12}$ alkyl, $M^+$=$Na^+$).

The composition can also include anionic alkyl sulfates and alkyl ether sulfate surfactants having branched alkyl chains which are synthesized from C8 to C18 branched alcohols which may be selected from the group consisting of: Guerbet alcohols, aldol condensation derived alcohols, oxo alcohols and mixtures thereof. Non-limiting examples of the 2-alkyl branched alcohols include oxo alcohols such as 2-methyl-1-undecanol, 2-ethyl-1-decanol, 2-propyl-1-nonanol, 2-butyl 1-octanol, 2-methyl-1-dodecanol, 2-ethyl-1-undecanol, 2-propyl-1-decanol, 2-butyl-1-nonanol, 2-pentyl-1-octanol, 2-pentyl-1-heptanol, and those sold under the tradenames LIAL® (Sasol), ISALCHEM® (Sasol), and NEODOL® (Shell), and Guerbet and aldol condensation derived alcohols such as 2-ethyl-1-hexanol, 2-propyl-1-butanol, 2-butyl-1-octanol, 2-butyl-1-decanol, 2-pentyl-1-nonanol, 2-hexyl-1-octanol, 2-hexyl-1-decanol and those sold under the tradename ISOFOL® (Sasol) or sold as alcohol ethoxylates and alkoxylates under the tradenames LUTENSOL XP® (BASF) and LUTENSOL XL® (BASF).

The anionic alkyl sulfates and alkyl ether sulfates may also include those synthesized from C8 to C18 branched alcohols derived from butylene or propylene which are sold under the trade names EXXAL™ (Exxon) and Marlipal® (Sasol). This includes anionic surfactants of the subclass of sodium trideceth-n sulfates (STnS), where n is between about 0.5 and about 3.5. Exemplary surfactants of this subclass are sodium trideceth-2 sulfates and sodium trideceth-3 sulfates. The composition of the present invention can also include sodium tridecyl sulfate.

The hair care composition may comprise a co-surfactant. The co-surfactant can be selected from the group consisting of amphoteric surfactant, zwitterionic surfactant, non-inonic surfactant and mixtures thereof. The co-surfactant can include, but is not limited to, lauramidopropyl betaine, cocoamidopropyl betaine, lauryl hydroxysultaine, sodium lauroamphoacetate, coco monoethanolamide and mixtures thereof.

The hair care composition comprises from about 1% to about 15%, from about 2% to about 12%, from about 3% to about 10%, from about 4% to about 8% by weight of one or more co-surfactants selected from the group consisting of amphoteric surfactant, zwitterionic surfactant, non-inonic surfactant and mixtures thereof.

Suitable amphoteric or zwitterionic surfactants for use in the hair care composition herein include those which are known for use in shampoo or other hair care cleansing. Non limiting examples of suitable zwitterionic or amphoteric surfactants are described in U.S. Pat. Nos. 5,104,646 and 5,106,609, which are incorporated herein by reference in their entirety.

Amphoteric co-surfactants suitable for use in the composition include those surfactants described as derivatives of aliphatic secondary and tertiary amines in which the aliphatic radical can be straight or branched chain and wherein one of the aliphatic substituents contains from about 8 to about 18 carbon atoms and one contains an anionic group such as carboxy, sulfonate, sulfate, phosphate, or phosphonate. Suitable amphoteric surfactant include, but are not limited to, those selected from the group consisting of: sodium cocaminopropionate, sodium cocaminodipropionate, sodium cocoamphoacetate, sodium cocoamphohydroxypropylsulfonate, sodium cocoamphopropionate, sodium comamphopropionate, sodium lauraminopropionate, sodium lauroamphoacetate, sodium lauroamphohydroxypropylsulfonate, sodium lauroamphopropionate, sodium cornamphopropionate, sodium lauriminodipropionate, ammonium cocaminopropionate, ammonium cocantinodipropionate, ammonium cocoamphoacetate, ammonium cocoamphohydroxypropylsulfonate, ammonium cocoamphopropionate, ammonium cornamphopropionate, ammonium lauraminopropionate, ammonium lauroamphoacetate, ammonium lauroamphohydroxypropylsulfonate, ammonium lauroamphopropionate, ammonium cornamphopropionate, ammonium lauriminodipropionate, triethanonlamine cocaminopropionate, triethanonlamine cocaminodipropionate, triethanonlamine cocoamphoacetate, triethanonlamine cocoamphohydroxypropylsulfonate, triethanonlamine cocoamphopropionate, triethanonlamine cornamphopropionate, triethanonlamine lauraminopropionate, triethanonlamine lauroamphoacetate, triethanonlamine lauroamphohydroxypropylsulfonate, triethanonlamine lauroamphopropionate, triethanonlamine cornamphopropionate, triethanonlamine lauriminodipropionate, cocoamphodipropionic acid, disodium caproamphodiacetate, disodium caproamphoadipropionate, disodium capryloamphodiacetate, disodium capryloamphodipriopionate, disodium cocoamphocarboxyethylhydroxypropylsulfate, disodium cocoantphodiacetate, disodium cocoamphodipropionate, disodium dicarboxyethylcocopropylenediamine, disodium laureth-5 carboxyamphodiacetate, disodium lauriminodipropionate, disodium lauroamphodiacetate, disodium lauroamphodipropionate, disodium oleoamphodipropionate, disodium PPG-2-isodecethyl-7 carboxyamphodiacetate, lauraminopropionic acid, lauroamphodipropionic acid, lauryl aminopropylglycine, lauryl diethylenediaminoglycine, and mixtures thereof The amphoteric co-surfactant can be a surfactant according to the following structure:

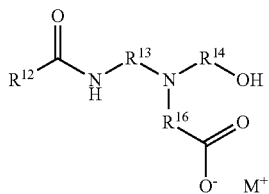

wherein R12 is a C-linked monovalent substituent selected from the group consisting of substituted alkyl systems comprising 9 to 15 carbon atoms, unsubstituted alkyl systems comprising 9 to 15 carbon atoms, straight alkyl systems comprising 9 to 15 carbon atoms, branched alkyl systems comprising 9 to 15 carbon atoms, and unsaturated alkyl systems comprising 9 to 15 carbon atoms; R13, R14, and R15 are each independently selected from the group consisting of C-linked divalent straight alkyl systems comprising 1 to 3 carbon atoms, and C-linked divalent branched alkyl systems comprising 1 to 3 carbon atoms; and is a monovalent counterion selected from the group consisting of sodium, ammonium and protonated triethanolamine. The amphoteric surfactant is selected from the group consisting of: sodium cocoamphoacetate, sodium cocoamphodiacetate, sodium lauroamphoacetate, sodium lauroamphodiacetate, ammonium lauroamphoacetate, ammonium cocoamphoacetate, triethanolamine lauroamphoacetate, triethanolamine cocoamphoacetate, and mixtures thereof.

The composition may comprise a zwitterionic co-surfactant, wherein the zwitterionic surfactant is a derivative of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group such as carboxy, sulfonate, sulfate, phosphate or phosphonate. The zwitterionic surfactant can be selected from the group consisting of: cocamidoethyl betaine, cocamidopropylamine oxide, cocamidopropyl betaine, cocamidopropyl dimethylaminohydroxypropyl hydrolyzed collagen, cocamidopropyldimonium hydroxypropyl hydrolyzed collagen, cocamidopropyl hydroxysultaine, cocobetaineamido amphopropionate, coco-betaine, coco-hydroxysultaine, coco/oleamidopropyl betaine, coco-sultaine, lauramidopropyl betaine, lauryl betaine, lauryl hydroxysultaine, lauryl sultaine, and mixtures thereof. A suitable zwitterionic surfactant is lauryl hydroxysultaine. The zwitterionic surfactant can be selected from the group consisting of: lauryl hydroxysultaine, cocamidopropyl hydroxysultaine, coco-betaine, coco-hydroxysultaine, coco-sultaine, lauryl betaine, lauryl sultaine, and mixtures thereof.

The co-surfactant can be a zwitterionic surfactant, wherein the zwitterionic surfactant is selected from the group consisting of: lauryl hydroxysultaine, cocamidopropyl hydroxysultaine, coco-betaine, coco-hydroxysultaine, coco-sultaine, lauryl betaine, lauryl sultaine, and mixtures thereof.

The co-surfactant can be a non-ionic surfactant selected from the group consisting of: Cocamide, Cocamide Methyl MEA, Cocamide DEA, Cocamide MEA, Cocamide MIPA, Lauramide DEA, Lauramide MEA, Lauramide MIPA, Myristamide DEA, Myristamide MEA, PEG-20 Cocamide MEA, PEG-2 Cocamide, PEG-3 Cocamide, PEG-4 Cocamide, PEG-5 Cocamide, PEG-6 Cocamide, PEG-7 Cocamide, PEG-3 Lauramide, PEG-5 Lauramide, PEG-3 Oleamide, PPG-2 Cocamide, PPG-2 Hydroxyethyl Cocamide, and mixtures thereof.

Suitable nonionic surfactants for use include those described in McCutcheion's Detergents and Emulsifiers, North American edition (1986), Allured Publishing Corp., and McCutcheion's Functional Materials, North American edition (1992). Suitable nonionic surfactants for use in the hair care compositions include, but are not limited to, polyoxyethylenated alkyl phenols, polyoxyethylenated alcohols, polyoxyethylenated polyoxypropylene glycols, glyceryl esters of alkanoic acids, polyglyceryl esters of alkanoic acids, propylene glycol esters of alkanoic acids, sorbitol esters of alkanoic acids, polyoxyethylenated sorbitor esters of alkanoic acids, polyoxyethylene glycol esters of alkanoic acids, polyoxyethylenated alkanoic acids, alkanolamides, N-alkylpyrrolidones, alkyl glycosides, alkyl polyglucosides, alkylamine oxides, and polyoxyethylenated silicones.

Representative polyoxyethylenated alcohols include alkyl chains ranging in the C9-C16 range and having from about 1 to about 110 alkoxy groups including, but not limited to, laureth-3, laureth-23, ceteth-10, steareth-10, steareth-100, beheneth-10, and commercially available from Shell Chemicals, Houston, Tex. under the trade names Neodol® 91, Neodol® 23, Neodol® 25, Neodol® 45, Neodol® 135, Neodo®l 67, Neodol® PC 100, Neodol® PC 200, Neodol® PC 600, and mixtures thereof.

Also available commercially are the polyoxyethylene fatty ethers available commercially under the Brij® trade name from Uniqema, Wilmington, Del., including, but not limited to, Brij® 30, Brij® 35, Brij® 52, Brij® 56, Brij® 58, Brij® 72, Brij® 76, Brij® 78, Brij® 93, Brij® 97, Brij® 98, Brij® 721 and mixtures thereof.

Suitable alkyl glycosides and alkyl polyglucosides can be represented by the formula (S)n-O—R wherein S is a sugar moiety such as glucose, fructose, mannose, galactose, and the like; n is an integer of from about 1 to about 1000, and R is a C8-C30 alkyl group. Examples of long chain alcohols from which the alkyl group can be derived include decyl alcohol, lauryl alcohol, myristyl alcohol, cetyl alcohol, stearyl alcohol, oleyl alcohol, and the like. Examples of these surfactants include alkyl polyglucosides wherein S is a glucose moiety, R is a C8-20 alkyl group, and n is an integer of from about 1 to about 9. Commercially available examples of these surfactants include decyl polyglucoside and lauryl polyglucoside available under trade names APG® 325 CS, APG® 600 CS and APG® 625 CS) from Cognis, Ambler, Pa. Also useful herein are sucrose ester surfactants such as sucrose cocoate and sucrose laurate and alkyl polyglucosides available under trade names Triton™ BG-10 and Triton™ CG-110 from The Dow Chemical Company, Houston, Tex.

Other nonionic surfactants suitable for use are glyceryl esters and polyglyceryl esters, including but not limited to, glyceryl monoesters, glyceryl monoesters of C12-22 saturated, unsaturated and branched chain fatty acids such as glyceryl oleate, glyceryl monostearate, glyceryl monopalmitate, glyceryl monobehenate, and mixtures thereof, and polyglyceryl esters of C12-22 saturated, unsaturated and branched chain fatty acids, such as polyglyceryl-4 isostearate, polyglyceryl-3 oleate, polyglyceryl-2-sesquioleate, triglyceryl diisostearate, diglyceryl monooleate, tetraglyceryl monooleate, and mixtures thereof.

Also useful herein as nonionic surfactants are sorbitan esters. Sorbitan esters of C12-22 saturated, unsaturated, and branched chain fatty acids are useful herein. These sorbitan esters usually comprise mixtures of mono-, di-, tri-, etc. esters. Representative examples of suitable sorbitan esters include sorbitan monolaurate (SPAN® 20), sorbitan monopalmitate (SPAN® 40), sorbitan monostearate (SPAN® 60), sorbitan tristearate (SPAN® 65), sorbitan monooleate (SPAN® 80), sorbitan trioleate (SPAN® 85), and sorbitan isostearate.

Also suitable for use herein are alkoxylated derivatives of sorbitan esters including, but not limited to, polyoxyethylene (20) sorbitan monolaurate (Tween® 20), polyoxyethylene (20) sorbitan monopalmitate (Tween® 40), polyoxyethylene (20) sorbitan monostearate (Tween® 60), polyoxyethylene (20) sorbitan monooleate (Tween® 80), polyoxyethylene (4) sorbitan monolaurate (Tween® 21), polyoxyethylene (4) sorbitan monostearate (Tween® 61), polyoxyethylene (5) sorbitan monooleate (Tween® 81), and mixtures thereof, all available from Uniqema.

Also suitable for use herein are alkylphenol ethoxylates including, but not limited to, nonylphenol ethoxylates (Tergitol™ NP-4, NP-6, NP-7, NP-8, NP-9, NP-10, NP-11, NP-12, NP-13, NP-15, NP-30, NP-40, NP-50, NP-55, NP-70 available from The Dow Chemical Company, Houston, Tex.) and octylphenol ethoxylates (Triton™ X-15, X-35, X-45, X-114, X-100, X-102, X-165, X-305, X-405, X-705 available from The Dow Chemical Company, Houston, Tex.).

Also suitable for use herein are alkanolamides including cocamide monoethanolamine (CMEA) and tertiary alkylamine oxides including lauramine oxide and cocamine oxide.

Nonionic surfactants useful herein have an HLB (hydrophile-lipophile balance) of at least 8, alternatively greater than 10, and alternatively greater than 12. The HLB represents the balance between the hydrophilic and lipophilic moieties in a surfactant molecule and is commonly used as a method of classification. The HLB values for commonly-used surfactants are readily available in the literature (e.g., HLB Index in McCutcheon's Emulsifiers and Detergents, MC Publishing Co., 2004).

Non limiting examples of other anionic, zwitterionic, amphoteric, and non-ionic additional surfactants suitable for use in the hair care composition are described in McCutcheon's, Emulsifiers and Detergents, 1989 Annual, published by M. C. Publishing Co., and U.S. Pat. Nos. 3,929,678, 2,658,072; 2,438,091; 2,528,378, which are incorporated herein by reference in their entirety.

The shampoo composition can comprise of 20-45 wt % detersive surfactant, from which 0-10 wt % is amphoteric surfactant, 2-25% is a sulfate having a branched alkyl carbon chain containing from C12 to C16 carbon atoms, 5-30 wt % is a sulfate having a linear alkyl carbon chain containing from C12 to C16 carbon atoms, a water-miscible solvent from about 2 wt % to about 8 wt %, and water carrier from about 40 wt % to about 80 wt %, wherein the ratio of linear anionic surfactant:Branched anionic surfactant is from about 0.4 to about 5.

The shampoo composition can comprise of 20-45 wt % detersive surfactant, from which 0-10 wt % is amphoteric surfactant, 6-30 wt % is a sulfate having a branched alkyl carbon chain containing from C12 to C16 carbon atoms, 0-20 wt % is a sulfate having a linear alkyl carbon chain containing from C12 to C16 carbon atoms, a water-miscible solvent from about 2 wt % to about 10 wt %, and water carrier from about 40 wt % to about 80 wt %, wherein the weight ratio of (Linear anionic surfactant/Branched anionic surfactant)/Miscible solvent is higher than about 0.2, and wherein the weight ratio of Branched anionic surfactant/Miscible solvent is higher than 5.

The shampoo composition can comprise of 5-45 wt % detersive surfactant, from which 5-35 wt % is anionic detersive surfactant, a water-miscible solvent from about 1 wt % to about 20 wt %, a hydrofluoro olefin foaming agent from about 3 wt % or higher, and water carrier from about 20 wt % to about 90 wt %, wherein the weight ratio of the foaming agent to Water-miscible solvent is lower than about 3.

The shampoo composition can comprise of 20-45 wt % detersive surfactant, from which 10-40 wt % is anionic detersive surfactant, 1-15 wt % of one or more co-surfactants selected from the group consisting of amphoteric, zwitterionic, nonionic and mixtures thereof; wherein about 1% or more are zwitterionic surfactants which possess a hydroxyl group in their molecular structure, from about 0.1% to about 35% by weight of one or more viscosity reducing agents, from about 0.05% to about 1% by weight of one or more cationic polymers with a weight average molecular weight of less than about 1,000,000 g/mol.

The shampoo composition can comprise of 20-45 wt % detersive surfactant, from which 10-40 wt % is anionic detersive surfactant, 1-15 wt % of one or more co-surfactants selected from the group consisting of lauryl hydroxysultaine, coco-hydroxysultaine, sodium lauroamphoacetate, sodium cocoamphoacetate, sodium lauroamphopropionate, sodium cocoamphopropionate, and mixture thereof, from about 0.1% to about 35% by weight of one or more viscosity reducing agents, from about 0.05% to about 1% by weight of one or more cationic polymers with a weight average molecular weight of less than about 1,000,000 g/mol.

Viscosity Reducing Agents

The hair care composition described herein may comprise from about 0.5% to about 15%, alternatively from about 0.75% to about 10.0%, alternatively from about 1% to about 7.5%, alternatively from about 1.25% to about 5.0%, and alternatively from about 1.5% to about 3.5% of a viscosity reducing agent, by weight of the hair care composition. Non-limiting examples of suitable viscosity reducing agents include water miscible solvents, hydrotropes, Class A materials, Class B materials, silicone polyethers, and mixtures thereof.

The hair care composition described herein may have a liquid phase viscosity of from about 8 centipoise to about 15,000 centipoise, alternatively from about 9 centipoise to about 12,000 centipoise, alternatively from about 10 centipoise to about 11,000 centipoise, alternatively from about 11 centipoise to about 5,000 centipoise, alternatively from about 12 centipoise to 2,500 centipoise, alternatively from about 13 centipoise to about 1,500 centipoise, and alternatively from about 14 centipoise to about 1,000 centipoise.

The hair composition viscosity values may be measured using a TA Instruments AR-G2 Rheometer with a concentric cylinder attachment at a shear rate of 100 reciprocal seconds at 25° C.

1. Water Miscible Solvents

The compositions can include water miscible glycols and other diols. Non-limiting examples include dipropylene glycol, tripropylene glycol, diethylene glycol, ethylene glycol, propylene glycol, glycerin, 1,3-propane diol, 2,2-propanediol, 1,2-butanediol, 1,3-butanediol, 1,4-butanediol, 2,3-butanediol, 2-methyl-2,4-pentanediol, and mixtures thereof. The hair care composition may comprise two or more water miscible solvents, wherein at least one of the solvents is dipropylene glycol.

2. Hydrotropes

The compositions can include hydrotropes. Non-limiting examples include lower aliphatic alcohols, lower alkylbenzene sulphonates (derivatives of xylene and toluene) and combinations of these. Preferred are alcohol, urea, sodium xylene sulphonate, ammonium xylene sulfonate, and potassium xylene sulfonate.

3. Class A Materials

The Class A viscosity reducing agents may have a partition dispersion coefficient of from about −5 to about −0.7, alternatively from about −4.6 to about −0.85, alternatively from about −4.5 to about −0.9, alternatively from about −3.1 to about −0.7, and alternatively from about −3 to about −0.85. The Class A viscosity reducing agents may have a partition dispersion coefficient of from about −4.6 to about −1.9, alternatively from about −4.5 to about −2, wherein the one or more viscosity reducing agents has at least 2 polar groups, or has 1 polar group and less than 5 acyclic sp3 hybridized carbon atoms that are connected to each other in a contiguous group. The Class A viscosity reducing agents may have a partition dispersion coefficient of from about −4.6 to about −1.9, alternatively from about −4.5 to about −2, wherein the one or more viscosity reducing agents has 2 to 4 polar groups, or has 1 polar group and 1 to 3 acyclic sp3 hybridized carbon atoms that are connected to each other in a contiguous group. The Class A viscosity reducing agents may have a partition dispersion coefficient of from about −4.6 to about −1.9, alternatively from about −4.5 to about −2, wherein the one or more viscosity reducing agents has 2 to 4 polar groups, or has 1 polar group and 2 acyclic sp3 hybridized carbon atoms that are connected to each other in a contiguous group. The Class A viscosity reducing agents may provide unexpected viscosity reduction when used in the hair care composition described herein.

The partition dispersion coefficient (PDC) is defined by the following equation:

$$PDC = \log P - 0.3001*(\delta D)2 + 10.362*\delta D - 93.251$$

wherein log P is the octanol water partitioning coefficient as computed by the Consensus algorithm implemented in ACD/Percepta version 14.02 by Advanced Chemistry Development, Inc. (ACD/Labs, Toronto, Canada), and wherein δD is the Hansen solubility dispersion parameter in (MPa)½ computed using Steven Abbott and Hiroshi Yamamoto's "HSPIP—Hansen Solubility Parameters in Practice" program, 4th Edition, version 4.1.07.

The viscosity reducing agents may be organic compounds comprising 1 polar group, alternatively at least 1 polar group, alternatively 2 to 4 polar groups, and alternative alternatively at least 2 polar groups. The polar groups may be selected from the group consisting of alcohols, aldehydes, esters, lactones, coumarins, ethers, ketones, phenol, phenyl, oxides, alkenyl, alkynyl, and combinations thereof. The viscosity reducing agents may have a molecular weight of between 100 daltons and 300 daltons, alternatively from about 125 daltons to about 300 daltons. Additionally, the viscosity reducing agents may have a water solubility at between 23 and 25 degrees Celsius of from about 900 to 50,000 mg/L.

The Class A viscosity reducing agents may be selected from the group consisting of raspberry ketone, triethyl citrate, 5-methyl-3-heptanone oxime, hydroxycitronellal, camphor gum, 2-isopropyl-5-methyl-2-hexenal, eucalyptol, 1,1-dimethoxyoctane, isobutyl hexanoate, dihyro iso jasmonate, and combinations thereof. Alternatively, the Class A viscosity reducing agents may be selected from the group consisting of raspberry ketone, triethyl citrate, hydroxycitronellal, ethanol, dipropylene glycol, and combinations thereof.

4. Class B Materials

The Class B viscosity reducing agents may have a partition dispersion coefficient of from about 0.05 to about 5.1, alternatively from about 0.08 to about 4.5, alternatively from about 0.09 to about 4.4, alternatively from about 0.05 to about 2.0, alternatively from about 0.08 to about 1.8, alternatively from about 0.09 to about 1.7, and alternatively from about 0.095 to about 1.68. The Class B viscosity reducing agents may provide unexpected viscosity reduction when used in the hair care composition described herein.

The partition dispersion coefficient (PDC) is defined by the following equation:

$$PDC = \log P - 0.3001*(\delta D)^2 + 10.362*\delta D - 93.251$$

wherein log P is the octanol water partitioning coefficient as computed by the Consensus algorithm implemented in ACD/Percepta version 14.02 by Advanced Chemistry Development, Inc. (ACD/Labs, Toronto, Canada), and wherein δD is the Hansen solubility dispersion parameter in (MPa)^{1/2} computed using Steven Abbott and Hiroshi Yamamoto's "HSPIP—Hansen Solubility Parameters in Practice" program, 4th Edition, version 4.1.07.

The viscosity reducing agents may be organic compounds comprising 1 polar group, alternatively at least 1 polar group, alternatively 2 to 4 polar groups, and alternative alternatively at least 2 polar groups. The polar groups may be selected from the group consisting of alcohols, aldehydes, esters, lactones, coumarins, ethers, ketones, phenol, phenyl, oxides, alkenyl, alkynyl, and combinations thereof. The viscosity reducing agents may have a molecular weight of between 100 daltons and 300 daltons, alternatively from about 125 daltons to about 300 daltons. Additionally, the viscosity reducing agents may have a water solubility at between 23 and 25 degrees Celsius of from about 10 to 900 mg/L.

The Class B viscosity reducing agents may be selected from the group consisting of veloutone, isoamyl salicylate, gamma-terpinene, linalyl iso butyrate, alpha-terpinene, limonene, dipentene, geranyl phenyl acetate, iso propyl myristate, hexadecane, and combinations thereof. Alternatively, the Class B viscosity reducing agents may be selected from the group consisting of veloutone, gamma-terpinene, linalyl iso butyrate, alpha-terpinene, limonene, dipentene, geranyl phenyl acetate, iso propyl myristate, hexadecane, and combinations thereof. Alternatively, the Class B viscosity reducing agents may be selected from the group consisting of veloutone, isoamyl salicylate, gamma-terpinene, linalyl iso butyrate, alpha-terpinene, limonene, dipentene, geranyl phenyl acetate, and combinations thereof.

5. Silicone Polyethers

The personal care composition may comprise silicone/PEG-8. Non-limiting examples include PEG-8 Dimethicone such as Silsurf A208 which has a MW of about 855, or Silsurf D208 which has MW of about 2706.

C. Water Carrier

The hair care compositions can include from about 45% to about 78%, alternatively from about 50% to about 75%, alternatively from about 55% to about 70%, alternatively from about 60% to about 68% water by weight of the hair care composition.

D. Cationic Polymers

The hair care composition can also comprise a cationic polymer. These cationic polymers can include at least one of (a) a cationic guar polymer, (b) a cationic non-guar galactomannan polymer, (c) a cationic tapioca polymer, (d) a cationic copolymer of acrylamide monomers and cationic monomers, and/or (e) a synthetic, non-crosslinked, cationic polymer, which may or may not form lyotropic liquid crystals upon combination with the detersive surfactant (f) a cationic cellulose polymer. Additionally, the cationic polymer can be a mixture of cationic polymers.

The hair care composition may comprise a cationic guar polymer, which is a cationically substituted galactomannan (guar) gum derivatives. Guar gum for use in preparing these guar gum derivatives is typically obtained as a naturally occurring material from the seeds of the guar plant. The guar molecule itself is a straight chain mannan, which is branched at regular intervals with single membered galactose units on alternative mannose units. The mannose units are linked to each other by means of β(1-4) glycosidic linkages. The galactose branching arises by way of an α(1-6) linkage. Cationic derivatives of the guar gums are obtained by reaction between the hydroxyl groups of the polygalactomannan and reactive quaternary ammonium compounds. The degree of substitution of the cationic groups onto the guar structure should be sufficient to provide the requisite cationic charge density described above.

The cationic polymer, including but not limited to a cationic guar polymer, can have a molecular weight of less than 1.0 million g/mol, or from about 10 thousand to about 1 million g/mol, or from about 25 thousand to about 1 million g/mol, or from about 50 thousand to about 1 million g/mol, or from about 100 thousand to about 1 million g/mol. The cationic guar polymer can have a charge density of from about 0.2 to about 2.2 meq/g, or from about 0.3 to about 2.0 meq/g, or from about 0.4 to about 1.8 meq/g; or from about 0.5 meq/g to about 1.7 meq/g.

The cationic guar polymer can have a weight average molecular weight of less than about 1.0 million g/mol, and has a charge density of from about 0.1 meq/g to about 2.5 meq/g. The cationic guar polymer can have a weight average molecular weight of less than 950 thousand g/mol, or from about 10 thousand to about 900 thousand g/mol, or from about 25 thousand to about 900 thousand g/mol, or from about 50 thousand to about 900 thousand g/mol, or from about 100 thousand to about 900 thousand g/mol. from about 150 thousand to about 800 thousand g/mol, The cationic guar polymer can have a charge density of from about 0.2 to about 2.2 meq/g, or from about 0.3 to about 2.0 meq/g, or from about 0.4 to about 1.8 meq/g; or from about 0.5 meq/g to about 1.5 meq/g.

The hair care composition can comprise from about 0.01% to about 1%, alternatively from about 0.05% to about 1%, alternatively from about 0.05% to about 0.9%, alternatively from about 0.1% to about 0.8%, or alternatively from about 0.2% to about 0.7% of cationic polymer (a), by total weight of the hair care composition.

The cationic guar polymer may be formed from quaternary ammonium compounds. The quaternary ammonium compounds for forming the cationic guar polymer can conform to the general formula 1:

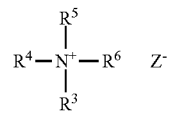

wherein where $R^3$, $R^4$ and $R^5$ are methyl or ethyl groups; $R^6$ is either an epoxyalkyl group of the general formula 2:

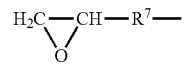

or $R^6$ is a halohydrin group of the general formula 3:

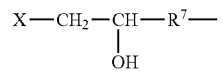

wherein $R^7$ is a $C_1$ to $C_3$ alkylene; X is chlorine or bromine, and Z is an anion such as Cl—, Br—, I— or $HSO_4$—.

The cationic guar polymer can conform to the general formula 4:

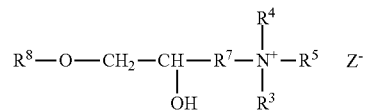

wherein $R^8$ is guar gum; and wherein $R^4$, $R^5$, $R^6$ and $R^7$ are as defined above; and wherein Z is a halogen. The cationic guar polymer can conform to Formula 5:

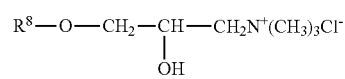

Suitable cationic guar polymers include cationic guar gum derivatives, such as guar hydroxypropyltrimonium chloride. The cationic guar polymer can be a guar hydroxypropyltrimonium chloride. Specific examples of guar hydroxypropyltrimonium chlorides include the Jaguar® series commercially available from Rhone-Poulenc Incorporated, for example Jaguar® C-500, commercially available from Rhodia. Jaguar® C-500 has a charge density of 0.8 meq/g and a molecular weight of 500,000 g/mol. Other suitable guar hydroxypropyltrimonium chloride are: guar hydroxypropyltrimonium chloride which has a charge density of about 1.1 meq/g and a molecular weight of about 500,000 g/mol is available from ASI, a charge density of about 1.5 meq/g and a molecular weight of about 500,000 g/mole is available from ASI. Other suitable guar hydroxypropyltrimonium chloride are: Hi-Care 1000, which has a charge density of about 0.7 meq/g and a Molecular weight of about 600,000 g/mole and is available from Rhodia; N-Hance 3269 and N-Hance 3270, which has a charge density of about 0.7 meq/g and a molecular weight of about 425,000 g/mol and is available from ASIAquaCat CG518 has a charge density of about 0.9 meq/g and a Molecular weight of about 50,000 g/mol and is available from ASI. BF-13, which is a borate (boron) free guar of charge density of about 1.1 meq/g and molecular weight of about 800,000 and BF-17, which is a borate (boron) free guar of charge density of about 1.7 meq/g and M. W.t of about 800,000 both available from ASI.

The hair care compositions may comprise a galactomannan polymer derivative having a mannose to galactose ratio of greater than 2:1 on a monomer to monomer basis, the galactomannan polymer derivative selected from the group consisting of a cationic galactomannan polymer derivative and an amphoteric galactomannan polymer derivative having a net positive charge. As used herein, the term "cationic galactomannan" refers to a galactomannan polymer to which a cationic group is added. The term "amphoteric galactomannan" refers to a galactomannan polymer to which a cationic group and an anionic group are added such that the polymer has a net positive charge.

Galactomannan polymers are present in the endosperm of seeds of the Leguminosae family. Galactomannan polymers are made up of a combination of mannose monomers and galactose monomers. The galactomannan molecule is a straight chain mannan branched at regular intervals with single membered galactose units on specific mannose units. The mannose units are linked to each other by means of β (1-4) glycosidic linkages. The galactose branching arises by way of an α (1-6) linkage. The ratio of mannose monomers to galactose monomers varies according to the species of the plant and also is affected by climate. Non Guar Galactomannan polymer derivatives suitable for use can have a ratio of mannose to galactose of greater than 2:1 on a monomer to monomer basis. Suitable ratios of mannose to galactose can be greater than about 3:1, and the ratio of mannose to galactose can be greater than about 4:1. Analysis of mannose to galactose ratios is well known in the art and is typically based on the measurement of the galactose content.

The gum for use in preparing the non-guar galactomannan polymer derivatives is typically obtained as naturally occurring material such as seeds or beans from plants. Examples of various non-guar galactomannan polymers include but are not limited to Tara gum (3 parts mannose/1 part galactose), Locust bean or Carob (4 parts mannose/1 part galactose), and *Cassia* gum (5 parts mannose/1 part galactose).

In The non-guar galactomannan polymer derivatives can have a M. Wt. from about 1,000 to about 1,000,000, and/or form about 5,000 to about 900,000.

The hair care compositions of the can also include galactomannan polymer derivatives which have a cationic charge density from about 0.5 meq/g to about 7 meq/g., The galactomannan polymer derivatives can have a cationic charge density from about 1 meq/g to about 5 meq/g. The degree of substitution of the cationic groups onto the galactomannan structure should be sufficient to provide the requisite cationic charge density.

The galactomannan polymer derivative can be a cationic derivative of the non-guar galactomannan polymer, which is obtained by reaction between the hydroxyl groups of the polygalactomannan polymer and reactive quaternary ammonium compounds. Suitable quaternary ammonium compounds for use in forming the cationic galactomannan polymer derivatives include those conforming to the general formulas 1-5, as defined above.

Cationic non-guar galactomannan polymer derivatives formed from the reagents described above are represented by the general formula 6:

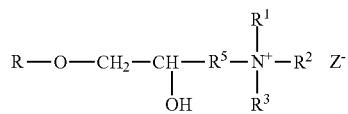

wherein R is the gum. The cationic galactomannan derivative can be a gum hydroxypropyltrimethylammonium chloride, which can be more specifically represented by the general formula 7:

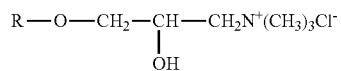

Alternatively the galactomannan polymer derivative can be an amphoteric galactomannan polymer derivative having a net positive charge, obtained when the cationic galactomannan polymer derivative further comprises an anionic group.

The cationic non-guar galactomannan can have a ratio of mannose to galactose is greater than about 4:1, a molecular weight of about 50,000 g/mol to about 1,000,000 g/mol, and/or from about 100,000 g/mol to about 900,000 g/mol and a cationic charge density from about 1 meq/g to about 5 meq/g, and/or from 2 meq/q to about 4 meq/q and can also be derived from a *cassia* plant.

The hair care compositions can comprise at least about 0.05% of a galactomannan polymer derivative by weight of the composition, alternatively from about 0.05% to about 2%, by weight of the composition, of a galactomannan polymer derivative.

The hair care compositions can comprise water-soluble cationically modified starch polymers. As used herein, the term "cationically modified starch" refers to a starch to which a cationic group is added prior to degradation of the starch to a smaller molecular weight, or wherein a cationic group is added after modification of the starch to achieve a desired molecular weight. The definition of the term "cationically modified starch" also includes amphoterically modified starch. The term "amphoterically modified starch" refers to a starch hydrolysate to which a cationic group and an anionic group are added.

The hair care compositions can comprise cationically modified starch polymers at a range of about 0.01% to about 10%, and/or from about 0.05% to about 5%, by weight of the composition.

The cationically modified starch polymers disclosed herein have a percent of bound nitrogen of from about 0.5% to about 4%.

The cationically modified starch polymers for use in the hair care compositions can have a molecular weight about 50,000 g/mol to about 1,000,000 g/mol and/or from about 100,000 g/mol to about 1,000,000 g/mol.

The hair care compositions can include cationically modified starch polymers which have a charge density of from about 0.2 meq/g to about 5 meq/g, and/or from about 0.2 meq/g to about 2 meq/g. The chemical modification to obtain such a charge density includes, but is not limited to, the addition of amino and/or ammonium groups into the starch molecules. Non-limiting examples of these ammonium groups may include substituents such as hydroxypropyl trimmonium chloride, trimethylhydroxypropyl ammonium chloride, dimethylstearylhydroxypropyl ammonium chloride, and dimethyldodecylhydroxypropyl ammonium chloride. See Solarek, D. B., Cationic Starches in Modified Starches: Properties and Uses, Wurzburg, O. B., Ed., CRC Press, Inc., Boca Raton, Fla. 1986, pp 113-125. The cationic groups may be added to the starch prior to degradation to a smaller molecular weight or the cationic groups may be added after such modification.

The cationically modified starch polymers generally have a degree of substitution of a cationic group from about 0.2 to about 2.5. As used herein, the "degree of substitution" of the cationically modified starch polymers is an average measure of the number of hydroxyl groups on each anhydroglucose unit which is derivatized by substituent groups. Since each anhydroglucose unit has three potential hydroxyl groups available for substitution, the maximum possible degree of substitution is 3. The degree of substitution is expressed as the number of moles of substituent groups per mole of anhydroglucose unit, on a molar average basis. The degree of substitution may be determined using proton nuclear magnetic resonance spectroscopy (".sup.1H NMR") methods well known in the art. Suitable .sup.1H NMR techniques include those described in "Observation on NMR Spectra of Starches in Dimethyl Sulfoxide, Iodine-Complexing, and Solvating in Water-Dimethyl Sulfoxide", Qin-Ji Peng and Arthur S. Perlin, Carbohydrate Research, 160 (1987), 57-72; and "An Approach to the Structural Analysis of Oligosaccharides by NMR Spectroscopy", J. Howard Bradbury and J. Grant Collins, Carbohydrate Research, 71, (1979), 15-25.

The source of starch before chemical modification can be chosen from a variety of sources such as tubers, legumes, cereal, and grains. Non-limiting examples of this source starch may include corn starch, wheat starch, rice starch, waxy corn starch, oat starch, cassaya starch, waxy barley, waxy rice starch, glutenous rice starch, sweet rice starch, amioca, potato starch, tapioca starch, oat starch, sago starch, sweet rice, or mixtures thereof.

The cationically modified starch polymers can be selected from degraded cationic maize starch, cationic tapioca, cationic potato starch, and mixtures thereof. Alternatively, the cationically modified starch polymers are cationic corn starch and cationic tapioca.

The starch, prior to degradation or after modification to a smaller molecular weight, may comprise one or more additional modifications. For example, these modifications may include cross-linking, stabilization reactions, phosphorylations, and hydrolyzations. Stabilization reactions may include alkylation and esterification.

The cationically modified starch polymers may be incorporated into the composition in the form of hydrolyzed starch (e.g., acid, enzyme, or alkaline degradation), oxidized starch (e.g., peroxide, peracid, hypochlorite, alkaline, or any other oxidizing agent), physically/mechanically degraded starch (e.g., via the thermo-mechanical energy input of the processing equipment), or combinations thereof.

An optimal form of the starch is one which is readily soluble in water and forms a substantially clear (% Transmittance.gtoreq.80 at 600 nm) solution in water. The transparency of the composition is measured by Ultra-Violet/Visible (UV/VIS) spectrophotometry, which determines the absorption or transmission of UV/VIS light by a sample, using a Gretag Macbeth Colorimeter Color i 5 according to the related instructions. A light wavelength of 600 nm has been shown to be adequate for characterizing the degree of clarity of cosmetic compositions.

Suitable cationically modified starch for use in hair care compositions are available from known starch suppliers. Also suitable for use in hair care compositions are nonionic modified starch that can be further derivatized to a cationically modified starch as is known in the art. Other suitable modified starch starting materials may be quaternized, as is known in the art, to produce the cationically modified starch polymer suitable for use in hair care compositions.

Starch Degradation Procedure: a starch slurry can be prepared by mixing granular starch in water. The temperature is raised to about 35° C. An aqueous solution of potassium permanganate is then added at a concentration of about 50 ppm based on starch. The pH is raised to about 11.5 with sodium hydroxide and the slurry is stirred sufficiently to prevent settling of the starch. Then, about a 30% solution of hydrogen peroxide diluted in water is added to a level of about 1% of peroxide based on starch. The pH of about 11.5 is then restored by adding additional sodium hydroxide. The reaction is completed over about a 1 to about 20 hour period. The mixture is then neutralized with dilute hydrochloric acid. The degraded starch is recovered by filtration followed by washing and drying.

The hair care composition can comprise a cationic copolymer of an acrylamide monomer and a cationic monomer, wherein the copolymer has a charge density of from about 1.0 meq/g to about 3.0 meq/g. The cationic copolymer can be a synthetic cationic copolymer of acrylamide monomers and cationic monomers.

The cationic copolymer can comprise:
(i) an acrylamide monomer of the following Formula AM:

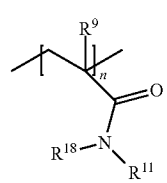

Formula AM where $R^9$ is H or $C_{1-4}$ alkyl; and $R^{10}$ and $R^{11}$ are independently selected from the group consisting of H, $C_{1-4}$ alkyl, $CH_2OCH_3$, $CH_2OCH_2CH(CH_3)_2$, and phenyl, or together are $C_{3-6}$cycloalkyl; and (ii) a cationic monomer conforming to Formula CM:

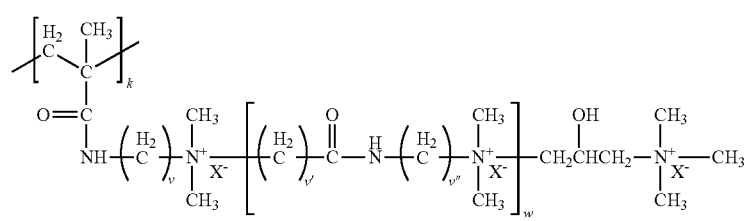

Formula CM where k=1, each of v, v', and v" is independently an integer of from 1 to 6, w is zero or an integer of from 1 to 10, and X⁻ is an anion.

The cationic monomer can conform to Formula CM and where k=1, v=3 and w=0, z=1 and X⁻ is Cl⁻ to form the following structure:

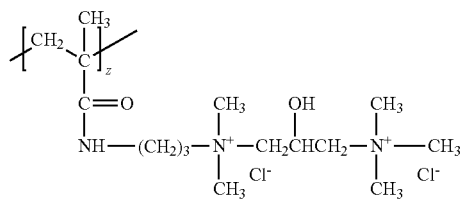

The above structure may be referred to as diquat. Alternatively, the cationic monomer can conform to Formula CM and wherein v and v" are each 3, v'=1, w=1, y=1 and X⁻ is Cl⁻, such as:

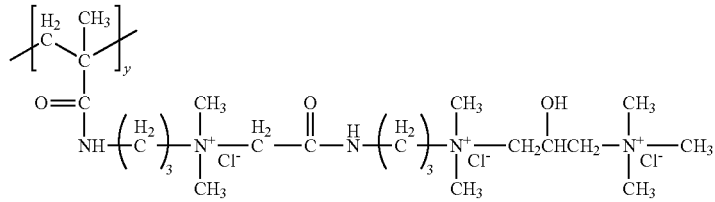

The above structure may be referred to as triquat.

Suitable acrylamide monomer include, but are not limited to, either acrylamide or methacrylamide.

The cationic copolymer is of an acrylamide monomer and a cationic monomer, wherein the cationic monomer is selected from the group consisting of: dimethylaminoethyl (meth)acrylate, dimethylaminopropyl (meth)acrylate, ditertiobutylaminoethyl (meth)acrylate, dimethylaminomethyl (meth)acrylamide, dimethylaminopropyl (meth)acrylamide; ethylenimine, vinylamine, 2-vinylpyridine, 4-vinylpyridine; trimethylammonium ethyl (meth)acrylate chloride, trimethylammonium ethyl (meth)acrylate methyl sulphate, dimethylammonium ethyl (meth)acrylate benzyl chloride, 4-benzoylbenzyl dimethylammonium ethyl acrylate chloride, trimethyl ammonium ethyl (meth)acrylamido chloride, trimethyl ammonium propyl (meth)acrylamido chloride, vinylbenzyl trimethyl ammonium chloride, diallyldimethyl ammonium chloride, and mixtures thereof.

The cationic copolymer can comprise a cationic monomer selected from the group consisting of: cationic monomers include trimethylammonium ethyl (meth)acrylate chloride, trimethylammonium ethyl (meth)acrylate methyl sulphate, dimethylammonium ethyl (meth)acrylate benzyl chloride, 4-benzoylbenzyl dimethylammonium ethyl acrylate chloride, trimethyl ammonium ethyl (meth)acrylamido chloride, trimethyl ammonium propyl (meth)acrylamido chloride, vinylbenzyl trimethyl ammonium chloride, and mixtures thereof.

The cationic copolymer can be water-soluble. The cationic copolymer is formed from (1) copolymers of (meth)acrylamide and cationic monomers based on (meth)acrylamide, and/or hydrolysis-stable cationic monomers, (2) terpolymers of (meth)acrylamide, monomers based on cationic (meth)acrylic acid esters, and monomers based on (meth)acrylamide, and/or hydrolysis-stable cationic monomers. Monomers based on cationic (meth)acrylic acid esters may be cationized esters of the (meth)acrylic acid containing a quaternized N atom. Cationized esters of the (meth)acrylic acid containing a quaternized N atom are quaternized dialkylaminoalkyl (meth)acrylates with C1 to C3 in the alkyl and alkylene groups. Suitable cationized esters of the (meth)acrylic acid containing a quaternized N atom can be selected from the group consisting of: ammonium salts of dimethylaminomethyl (meth)acrylate, dimethylaminoethyl (meth)acrylate, dimethylaminopropyl (meth)acrylate, diethylaminomethyl (meth)acrylate, diethylaminoethyl (meth)acrylate; and diethylaminopropyl (meth)acrylate quaternized with methyl chloride. The cationized esters of the (meth)acrylic acid containing a quaternized N atom is dimethylaminoethyl acrylate, which is quaternized with an alkyl halide, or with methyl chloride or benzyl chloride or dimethyl sulfate (ADAME-Quat). the cationic monomer when based on (meth)acrylamides can be quaternized dialkylaminoalkyl (meth)acrylamides with C1 to C3 in the alkyl and alkylene groups, or dimethylaminopropylacrylamide, which is quaternized with an alkyl halide, or methyl chloride or benzyl chloride or dimethyl sulfate.

Suitable cationic monomer based on a (meth)acrylamide include quaternized dialkylaminoalkyl(meth)acrylamide with C1 to C3 in the alkyl and alkylene groups. The cationic monomer based on a (meth)acrylamide can be dimethylaminopropylacrylamide, which is quaternized with an alkyl halide, especially methyl chloride or benzyl chloride or dimethyl sulfate.

The cationic monomer can be a hydrolysis-stable cationic monomer. Hydrolysis-stable cationic monomers can be, in addition to a dialkylaminoalkyl(meth)acrylamide, all monomers that can be regarded as stable to the OECD hydrolysis test. The cationic monomer can be hydrolysis-stable and the hydrolysis-stable cationic monomer can be selected from the group consisting of: diallyldimethylammonium chloride and water-soluble, cationic styrene derivatives.

The cationic copolymer can be a terpolymer of acrylamide, 2-dimethylammoniumethyl (meth)acrylate quaternized with methyl chloride (ADAME-Q) and 3-dimethylammoniumpropyl(meth)acrylamide quaternized with methyl chloride (DIMAPA-Q). The cationic copolymer can be formed from acrylamide and acrylamidopropyltrimethylammonium chloride, wherein the acrylamidopropyltrimethylammonium chloride has a charge density of from about 1.0 meq/g to about 3.0 meq/g.

The cationic copolymer can have a charge density of from about 1.1 meq/g to about 2.5 meq/g, or from about 1.1 meq/g to about 2.3 meq/g, or from about 1.2 meq/g to about 2.2 meq/g, or from about 1.2 meq/g to about 2.1 meq/g, or from about 1.3 meq/g to about 2.0 meq/g, or from about 1.3 meq/g to about 1.9 meq/g.

The cationic copolymer can have a molecular weight from about 10 thousand g/mol to about 1 million g/mol, or from about 25 thousand g/mol to about 1 million g/mol, or from about 50 thousand g/mol to about 1 million g/mol, or from about 100 thousand g/mol to about 1.0 million g/mol, or from about 150 thousand g/mol to about 1.0 million g/mol.

(a) Cationic Synthetic Polymers

The hair care composition can comprise a cationic synthetic polymer that may be formed from i) one or more cationic monomer units, and optionally ii) one or more monomer units bearing a negative charge, and/or iii) a nonionic monomer, wherein the subsequent charge of the copolymer is positive. The ratio of the three types of monomers is given by "m", "p" and "q" where "m" is the number of cationic monomers, "p" is the number of monomers bearing a negative charge and "q" is the number of nonionic monomers The cationic polymers can be water soluble or dispersible, non-crosslinked, and synthetic cationic polymers having the following structure:

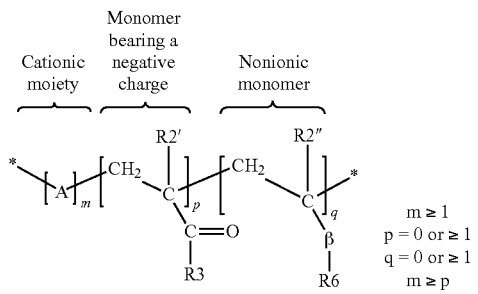

where A, may be one or more of the following cationic moieties:

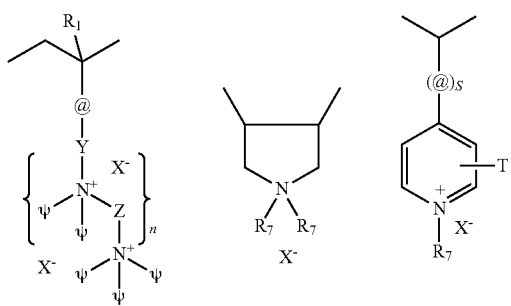

where @=amido, alkylamido, ester, ether, alkyl or alkylaryl;
where Y=C1-C22 alkyl, alkoxy, alkylidene, alkyl or aryloxy;
where ψ=C1-C22 alkyl, alkyloxy, alkyl aryl or alkyl arylox;
where Z=C1-C22 alkyl, alkyloxy, aryl or aryloxy;
where R1=H, C1-C4 linear or branched alkyl;
where s=0 or 1, n=0 or ≥1;
where T and $R_7$=C1-C22 alkyl; and
where X—=halogen, hydroxide, alkoxide, sulfate or alkylsulfate.

Where the monomer bearing a negative charge is defined by R2'=H, C1-C4 linear or branched alkyl and R3 as:

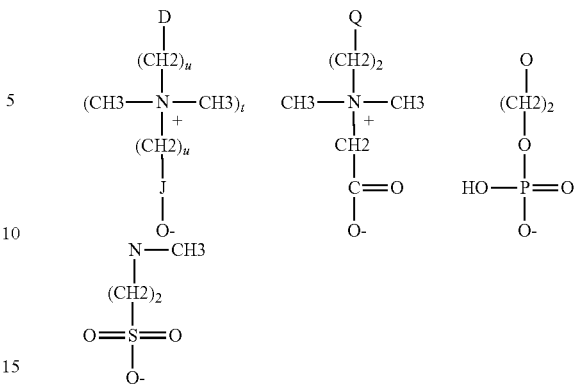

where D=O, N, or S;
where Q=$NH_2$ or O;
where u=1-6;
where t=0-1; and
where J=oxygenated functional group containing the following elements P, S, C.

Where the nonionic monomer is defined by R2"=H, C1-C4 linear or branched alkyl, R6=linear or branched alkyl, alkyl aryl, aryl oxy, alkyloxy, alkylaryl oxy and β is defined as

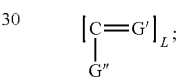

and where G' and G" are, independently of one another, O, S or N—H and L=0 or 1.

Examples of cationic monomers include aminoalkyl (meth)acrylates, (meth)aminoalkyl (meth)acrylamides; monomers comprising at least one secondary, tertiary or quaternary amine function, or a heterocyclic group containing a nitrogen atom, vinylamine or ethylenimine; diallyldialkyl ammonium salts; their mixtures, their salts, and macromonomers deriving from therefrom.

Further examples of cationic monomers include dimethylaminoethyl (meth)acrylate, dimethylaminopropyl (meth)acrylate, ditertiobutylaminoethyl (meth)acrylate, dimethylaminomethyl (meth)acrylamide, dimethylaminopropyl (meth)acrylamide, ethylenimine, vinylamine, 2-vinylpyridine, 4-vinylpyridine, trimethylammonium ethyl (meth)acrylate chloride, trimethylammonium ethyl (meth)acrylate methyl sulphate, dimethylammonium ethyl (meth)acrylate benzyl chloride, 4-benzoylbenzyl dimethylammonium ethyl acrylate chloride, trimethyl ammonium ethyl (meth)acrylamido chloride, trimethyl ammonium propyl (meth)acrylamido chloride, vinylbenzyl trimethyl ammonium chloride, diallyldimethyl ammonium chloride.

Suitable cationic monomers include those which comprise a quaternary ammonium group of formula —$NR_3^+$, wherein R, which is identical or different, represents a hydrogen atom, an alkyl group comprising 1 to 10 carbon atoms, or a benzyl group, optionally carrying a hydroxyl group, and comprise an anion (counter-ion). Examples of anions are halides such as chlorides, bromides, sulphates, hydrosulphates, alkylsulphates (for example comprising 1 to 6 carbon atoms), phosphates, citrates, formates, and acetates.

Suitable cationic monomers include trimethylammonium ethyl (meth)acrylate chloride, trimethylammonium ethyl (meth)acrylate methyl sulphate, dimethylammonium ethyl (meth)acrylate benzyl chloride, 4-benzoylbenzyl dimethylammonium ethyl acrylate chloride, trimethyl ammonium ethyl (meth)acrylamido chloride, trimethyl ammonium propyl (meth)acrylamido chloride, vinylbenzyl trimethyl ammonium chloride.

Additional suitable cationic monomers include trimethyl ammonium propyl (meth)acrylamido chloride.

Examples of monomers bearing a negative charge include alpha ethylenically unsaturated monomers comprising a phosphate or phosphonate group, alpha ethylenically unsaturated monocarboxylic acids, monoalkylesters of alpha ethylenically unsaturated dicarboxylic acids, monoalkylamides of alpha ethylenically unsaturated dicarboxylic acids, alpha ethylenically unsaturated compounds comprising a sulphonic acid group, and salts of alpha ethylenically unsaturated compounds comprising a sulphonic acid group.

Suitable monomers with a negative charge include acrylic acid, methacrylic acid, vinyl sulphonic acid, salts of vinyl sulfonic acid, vinylbenzene sulphonic acid, salts of vinylbenzene sulphonic acid, alpha-acrylamidomethylpropanesulphonic acid, salts of alpha-acrylamidomethylpropanesulphonic acid, 2-sulphoethyl methacrylate, salts of 2-sulphoethyl methacrylate, acrylamido-2-methylpropanesulphonic acid (AMPS), salts of acrylamido-2-methylpropanesulphonic acid, and styrenesulphonate (SS).

Examples of nonionic monomers include vinyl acetate, amides of alpha ethylenically unsaturated carboxylic acids, esters of an alpha ethylenically unsaturated monocarboxylic acids with an hydrogenated or fluorinated alcohol, polyethylene oxide (meth)acrylate (i.e. polyethoxylated (meth) acrylic acid), monoalkylesters of alpha ethylenically unsaturated dicarboxylic acids, monoalkylamides of alpha ethylenic ally unsaturated dicarboxylic acids, vinyl nitriles, vinylamine amides, vinyl alcohol, vinyl pyrolidone, and vinyl aromatic compounds.

Suitable nonionic monomers include styrene, acrylamide, methacrylamide, acrylonitrile, methylacrylate, ethylacrylate, n-propylacrylate, n-butylacrylate, methylmethacrylate, ethylmethacrylate, n-propylmethacrylate, n-butylmethacrylate, 2-ethyl-hexyl acrylate, 2-ethyl-hexyl methacrylate, 2-hydroxyethylacrylate and 2-hydroxyethylmethacrylate.

The anionic counterion (X—) in association with the synthetic cationic polymers may be any known counterion so long as the polymers remain soluble or dispersible in water, in the hair care composition, or in a coacervate phase of the hair care composition, and so long as the counterions are physically and chemically compatible with the essential components of the hair care composition or do not otherwise unduly impair product performance, stability or aesthetics. Non limiting examples of such counterions include halides (e.g., chlorine, fluorine, bromine, iodine), sulfate and methylsulfate.

The concentration of the cationic polymers ranges about 0.025% to about 5%, from about 0.1% to about 3%, and/or from about 0.2% to about 1%, by weight of the hair care composition.

Suitable cationic cellulose polymers are salts of hydroxyethyl cellulose reacted with trimethyl ammonium substituted epoxide, referred to in the industry (CTFA) as Polyquaternium 10 and available from Dow/Amerchol Corp. (Edison, N.J., USA) in their Polymer LR, JR, and KG series of polymers. Other suitable types of cationic cellulose include the polymeric quaternary ammonium salts of hydroxyethyl cellulose reacted with lauryl dimethyl ammonium-substituted epoxide referred to in the industry (CTFA) as Polyquaternium 24. These materials are available from Dow/Amerchol Corp. under the tradename Polymer LM-200. Other suitable types of cationic cellulose include the polymeric quaternary ammonium salts of hydroxyethyl cellulose reacted with lauryl dimethyl ammonium-substituted epoxide and trimethyl ammonium substituted epoxide referred to in the industry (CTFA) as Polyquaternium 67. These materials are available from Dow/Amerchol Corp. under the tradename SoftCAT Polymer SL-5, SoftCAT Polymer SL-30, Polymer SL-60, Polymer SL-100, Polymer SK-L, Polymer SK-M, Polymer SK-MH, and Polymer SK-H.

E. Conditioning Agents

The hair care compositions may comprise one or more conditioning agent. Conditioning agents include materials that are used to give a particular conditioning benefit to hair and/or skin. The conditioning agents useful in the hair care compositions of the present invention typically comprise a water-insoluble, water-dispersible, non-volatile, liquid that forms emulsified, liquid particles. Suitable conditioning agents for use in the hair care composition are those conditioning agents characterized generally as silicones (e.g., silicone oils, cationic silicones, silicone gums, high refractive silicones, and silicone resins), organic conditioning oils (e.g., hydrocarbon oils, polyolefins, and fatty esters) or combinations thereof, or those conditioning agents which otherwise form liquid, dispersed particles in the aqueous surfactant matrix.

1. Silicone Conditioning Agents

The hair care composition can comprise from about 0% to about 20% by weight, alternatively from about 6% to about 18% by weight; and alternatively from about 8% to about 16% by weight of one of more silicones with a particle size of less than about 300 nm, alternatively less than about 200 nm, and alternatively less than about 100 nm. The silicone can be in the form of a nanoemulsion.

The particle size of the one or more silicones may be measured by dynamic light scattering (DLS). A Malvern Zetasizer Nano ZEN3600 system (www.malvern.com) using He—Ne laser 633 nm may be used for the measurement at 25° C.

The autocorrelation function may be analyzed using the Zetasizer Software provided by Malvern Instruments, which determines the effective hydrodynamic radius, using the Stokes-Einstein equation:

$$D = \frac{k_g T}{6\pi \eta R}$$

wherein $k_B$ is the Boltzmann Constant, T is the absolute temperature, $\eta$ is the viscosity of the medium, D is the mean diffusion coefficient of the scattering species, and R is the hydrodynamic radius of particles.

Particle size (i.e. hydrodynamic radius) may be obtained by correlating the observed speckle pattern that arises due to Brownian motion and solving the Stokes-Einstein equation, which relates the particle size to the measured diffusion constant, as is known in the art.

For each sample, 3 measurements may be made and Z-average values may be reported as the particle size.

The one or more silicones may be in the form of a nanoemulsion. The nanoemulsion may comprise any silicone suitable for application to the skin and/or hair.

The one or more silicones may include in their molecular structure polar functional groups such as Si—OH (present in dimethiconols), primary amines, secondary amines, tertiary amines, and quaternary ammonium salts. The one or more silicones may be selected from the group consisting of aminosilicones, pendant quaternary ammonium silicones, terminal quaternary ammonium silicones, amino polyalkylene oxide silicones, quaternary ammonium polyalkylene oxide silicones, and amino morpholino silicones.

The one or more silicones may comprise:
(a) at least one aminosilicone corresponding to formula (V):

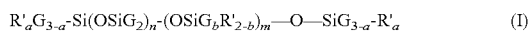   (I)

in which:
G is chosen from a hydrogen atom, a phenyl group, OH group, and $C_1$-$C_8$ alkyl groups, for example methyl,
a is an integer ranging from 0 to 3, and alternatively a is 0,
b is chosen from 0 and 1, and alternatively b is 1,
m and n are numbers such that the sum (n+m) can range for example from 1 to 2 000, such as for example from 50 to 150, wherein n can be for example chosen from numbers ranging from 0 to 1 999, such as for example from 49 to 149, and wherein m can be chosen from numbers ranging for example from 1 to 2 000, such as for example from 1 to 10;
R' is a monovalent group of formula —$C_qH_{2q}$L in which q is a number from 2 to 8 and L is an optionally quaternized amine group chosen from the groups:
—NR"—$CH_2$—$CH_2$—N'($R^1$)$_2$,
—N(R")$_2$,
—$N^+$(R")$_3$$A^-$,
—$N^+$H(R")$_2$$A^-$,

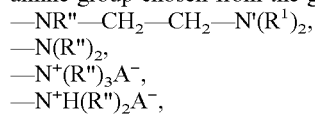

—$N^+H_2$(R")$A^-$, and
—N(R")—$CH_2$—$CH_2$—$N^+$R"$H_2$$A^-$,
in which R" can be chosen from a hydrogen atom, phenyl groups, benzyl groups, and saturated monovalent hydrocarbon-based groups, such as for example an alkyl group comprising from 1 to 20 carbon atoms, and $A^-$ is chosen from halide ions such as, for example, fluoride, chloride, bromide and iodide.

The one or more silicones may include those corresponding to formula (1) wherein a=0, G=methyl, m and n are numbers such that the sum (n+m) can range for example from 1 to 2 000, such as for example from 50 to 150, wherein n can be for example chosen from numbers ranging from 0 to 1 999, such as for example from 49 to 149, and wherein m can be chosen from numbers ranging for example from 1 to 2 000, such as for example from 1 to 10; and L is —N(CH$_3$)$_2$ or —NH$_2$, alternatively —NH$_2$.

Additional said at least one aminosilicone of the invention include:
(b) pendant quaternary ammonium silicones of formula (VII):

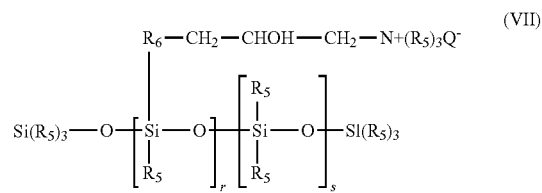   (VII)

in which:
$R_5$ is chosen from monovalent hydrocarbon-based groups comprising from 1 to 18 carbon atoms, such as $C_1$-$C_{18}$ alkyl groups and $C_2$-$C_{18}$ alkenyl groups, for example methyl;
$R_6$ is chosen from divalent hydrocarbon-based groups, such as divalent $C_1$-$C_{18}$ alkylene groups and divalent $C_1$-$C_{18}$ alkylenoxy groups, for example $C_1$-$C_8$ alkylenoxy groups, wherein said $R_6$ is bonded to the Si by way of an SiC bond;
$Q^-$ is an anion that can be for example chosen from halide ions, such as chloride, and organic acid salts (such as acetate);
r is an average statistical value ranging from 2 to 20, such as from 2 to 8;
s is an average statistical value ranging from 20 to 200, such as from 20 to 50.

Such aminosilicones are described more particularly in U.S. Pat. No. 4,185,087, the disclosure of which is incorporated by reference herein.

A silicone which falls within this class is the silicone sold by the company Union Carbide under the name "Ucar Silicone ALE 56".

Further examples of said at least one aminosilicone include:
c) quaternary ammonium silicones of formula (VIIb):

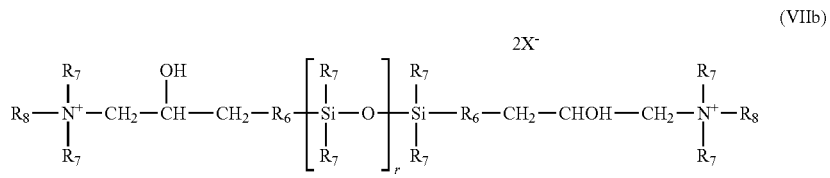   (VIIb)

in which:
groups $R_7$, which may be identical or different, are each chosen from monovalent hydrocarbon-based groups comprising from 1 to 18 carbon atoms, such as $C_1$-$C_{18}$ alkyl groups, for example methyl, $C_2$-$C_{18}$ alkenyl groups, and rings comprising 5 or 6 carbon atoms;
$R_6$ is chosen from divalent hydrocarbon-based groups, such as divalent $C_1$-$C_{18}$ alkylene groups and divalent $C_1$-$C_{18}$alkylenoxy, for example $C_1$-$C_8$, group connected to the Si by an SiC bond;
$R_8$, which may be identical or different, represent a hydrogen atom, a monovalent hydrocarbon-based group comprising from 1 to 18 carbon atoms, and in particular a $C_1$-$C_{18}$ alkyl group, a $C_2$-$C_{18}$ alkenyl group or a group —$R_6$—NHCOR$_7$;
$X^-$ is an anion such as a halide ion, in particular chloride, or an organic acid salt (acetate, etc.);
r represents an average statistical value from 2 to 200 and in particular from 5 to 100.

Such silicones are described, for example, in application EP-A-0 530 974, the disclosure of which is incorporated by reference herein.

Silicones falling within this class are the silicones sold by the company Eovnik under the names Abil Quat 3270, Abil Quat 3272, Abil Quat 3474 and Abil ME 45.

Further examples of said at least one aminosilicone include:

d) quaternary ammonium and polyalkylene oxide silicones wherein the quaternary nitrogen groups are located in the polysiloxane backbone, at the termini, or both.

Such silicones are described in PCT Publication No. WO 2002/010257, the disclosure of which is incorporated by reference herein.

Silicones falling within this class are the silicones sold by the company Momentive under the names Silsoft Q.

(e) Aminofunctional silicones having morpholino groups of formula (V):

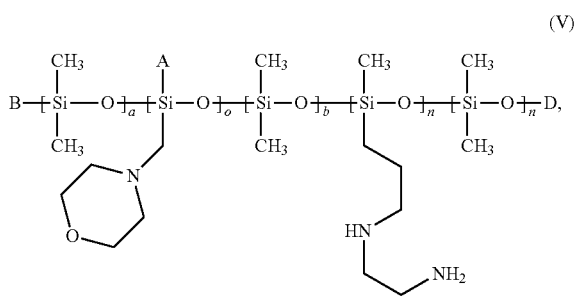

in which

A denotes a structural unit (I), (II), or (III) bound via —O—

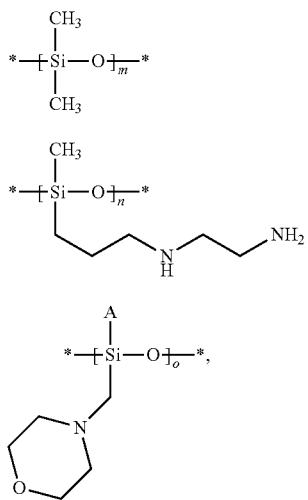

or an oligomeric or polymeric residue, bound via —O—, containing structural units of formulas (I), (II), or (III), or half of a connecting oxygen atom to a structural unit (III), or denotes —OH,

* denotes a bond to one of the structural units (I), (II), or (III), or denotes a terminal group B (Si-bound) or D (O-bound), B denotes an —OH, —O—Si(CH$_3$)$_3$, —O—Si(CH$_3$)$_2$OH, —O—Si(CH$_3$)$_2$OCH$_3$ group, D denotes an —H, —Si(CH$_3$)$_3$, —Si(CH$_3$)$_2$OH, —Si(CH$_3$)$_2$OCH$_3$ group, a, b, and c denote integers between 0 and 1000, with the provision that a+b+c>0, m, n, and o denote integers between 1 and 1000.

Aminofunctional silicones of this kind bear the INCI name: Amodimethicone/Morpholinomethyl Silsesquioxane Copolymer. A particularly suitable amodimethicone is the product having the commercial name Wacker Belsil® ADM 8301E.

Examples of such silicones are available from the following suppliers:

offered by the company Dow Corning: Fluids: 2-8566, AP 6087, AP 6088, DC 8040 Fluid, fluid 8822A DC, DC 8803 & 8813 polymer, 7-6030, AP-8104, AP 8201; Emulsions: CE-8170 AF Micro Emulsion, 2-8177, 2-8194 Microemulsion, 9224 Emulsion, 939, 949, 959, DC 5-7113 Quat Microemulsion, DC 5-7070 Emulsion, DC CE-8810, CE 8401 Emulsion, CE 1619, Dow Corning Toray SS-3551, Dow Corning Toray SS-3552;

offered by the company Wacker: Wacker Belsil ADM 652, ADM 656, 1100, 1600, 1650 (fluids) ADM 6060 (linear amodimethicone) emulsion; ADM 6057 E (branched amodimethicone) emulsion; ADM 8020 VP (micro emulsion); SLM 28040 (micro emulsion);

offered by the Company Momentive: Silsoft 331, SF1708, SME 253 & 254 (emulsion), SM2125 (emulsion), SM 2658 (emulsion), Silsoft Q (emulsion)

offered by the company Shin-Etsu: KF-889, KF-8675, KF-8004, X-52-2265 (emulsion);

offered by the Company Siltech Silicones: Siltech E-2145, E-Siltech 2145-35;

offered by the company Evonik Industries: Abil T Quat 60th

Some non-limiting examples of aminosilicones include the compounds having the following INCI names: Silicone Quaternium-1, Silicone Quaternium-2, Silicone Quaternium-3, Silicone Quaternium-4, Silicone Quaternium-5, Silicone Quaternium-6, Silicone Quaternium-7, Silicone Quaternium-8, Silicone Quaternium-9, Silicone Quaternium-10, Silicone Quaternium-11, Silicone Quaternium-12, Silicone Quaternium-15, Silicone Quaternium-16, Silicone Quaternium -17, Silicone Quaternium-18, Silicone Quaternium-20, Silicone Quaternium-21, Silicone Quaternium-22, Quaternium-80, as well as Silicone Quaternium-2 Panthenol Succinate and Silicone Quaternium-16/Glycidyl Dimethicone Crosspolymer.

The aminosilicones can be supplied in the form of a nanoemulsion and include MEM 9049, MEM 8177, MEM 0959, MEM 8194, SME 253, and Silsoft Q.

The one or more silicones may include dimethicones, and/or dimethiconols. The dimethiconols are hydroxyl terminated dimethylsilicones represented by the general chemical formulas

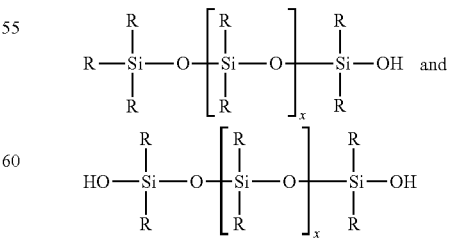

wherein R is an alkyl group (preferably R is methyl or ethyl, more preferably methyl) and x is an integer up to about 500, chosen to achieve the desired molecular weight. Commercial dimethiconols typically are sold as mixtures with dimethicone or cyclomethicone (e.g., Dow Corning® 1401, 1402, and 1403 fluids).

2. Non-Silicone Conditioning Agents

The conditioning agent of the hair care compositions described herein may also comprise at least one organic conditioning agents, either alone or in combination with other conditioning agents, such as the silicones described above. Non-limiting examples of organic conditioning agents are described below.

a. Hydrocarbon Oils

Suitable organic conditioning agents for use as conditioning agents in hair care compositions include, but are not limited to, hydrocarbon oils having at least about 10 carbon atoms, such as cyclic hydrocarbons, straight chain aliphatic hydrocarbons (saturated or unsaturated), and branched chain aliphatic hydrocarbons (saturated or unsaturated), including polymers and mixtures thereof. Straight chain hydrocarbon oils can be from about $C_{12}$ to about $C_{19}$. Branched chain hydrocarbon oils, including hydrocarbon polymers, typically will contain more than 19 carbon atoms.

b. Polyolefins

Organic conditioning oils for use in the hair care compositions described herein also include liquid polyolefins, including liquid poly-α-olefins and/or hydrogenated liquid poly-α-olefins. Polyolefins for use herein are prepared by polymerization of $C_4$ to about $C_{14}$ olefenic monomers, and alternatively from about $C_6$ to about $C_{12}$.

c. Fatty Esters

Other suitable organic conditioning agents for use as a conditioning agent in the hair care compositions described herein include fatty esters having at least 10 carbon atoms. These fatty esters include esters with hydrocarbyl chains derived from fatty acids or alcohols. The hydrocarbyl radicals of the fatty esters hereof may include or have covalently bonded thereto other compatible functionalities, such as amides and alkoxy moieties (e.g., ethoxy or ether linkages, etc.). Other oligomeric or polymeric esters, prepared from unsaturated glyceryl esters can also be used as conditioning materials.

d. Fluorinated Conditioning Compounds

Fluorinated compounds suitable for delivering conditioning to hair as organic conditioning agents include perfluoropolyethers, perfluorinated olefins, fluorine based specialty polymers that may be in a fluid or elastomer form similar to the silicone fluids previously described, and perfluorinated dimethicones.

e. Fatty Alcohols

Other suitable organic conditioning oils for use in the hair care compositions described herein include, but are not limited to, fatty alcohols having at least about 10 carbon atoms, about 10 to about 22 carbon atoms, and alternatively from about 12 to about 16 carbon atoms.

f. Alkyl Glucosides and Alkyl Glucoside Derivatives

Suitable organic conditioning oils for use in the hair care compositions described herein include, but are not limited to, alkyl glucosides and alkyl glucoside derivatives. Specific non-limiting examples of suitable alkyl glucosides and alkyl glucoside derivatives include Glucam E -10, Glucam E-20, Glucam P-10, and Glucquat 125 commercially available from Amerchol.

g. Polyethylene Glycols

Additional compounds useful herein as conditioning agents include polyethylene glycols and polypropylene glycols having a molecular weight of up to about 2,000,000 such as those with CTFA names PEG-200, PEG-400, PEG-600, PEG-1000, PEG-2M, PEG-7M, PEG-14M, PEG-45M and mixtures thereof.

F. Mechanical Foam Dispenser

The mechanical foam dispenser described herein may be selected from the group consisting of squeeze foam dispensers, pump foam dispensers, other mechanical foam dispensers, and combinations thereof. The mechanical foam dispenser can be a squeeze foam dispenser. Non-limiting examples of suitable pump dispensers include those described in WO 2004/078903, WO 2004/078901, and WO 2005/078063 and may be supplied by Albea (60 Electric Ave., Thomaston, Conn. 06787 USA) or Rieke Packaging Systems (500 West Seventh St., Auburn, Ind. 46706).

The mechanical foam dispenser may comprise a reservoir for holding the hair care composition. The reservoir may be made out of any suitable material selected from the group consisting of plastic, metal, alloy, laminate, and combinations thereof. The reservoir may be a refillable reservoir such as a pour-in or screw-on reservoir, or the reservoir may be for one-time use. The reservoir may also be removable from the mechanical foam dispenser. Alternatively, the reservoir may be integrated with the mechanical foam dispenser. Alternatively, there may be two or more reservoirs.

The reservoir may be comprised of a material selected from the group consisting of rigid materials, flexible materials, and combinations thereof. The reservoir may be comprised of a rigid material if it does not collapse under external atmospheric pressure when it is subject to an interior partial vacuum.

G. Aerosol Foam Dispenser

The aerosol foam dispenser may comprise a reservoir for holding the hair care composition. The reservoir may be made out of any suitable material selected from the group consisting of plastic, metal, alloy, laminate, and combinations thereof. The reservoir may be for one-time use. The reservoir may be removable from the aerosol foam dispenser. Alternatively, the reservoir may be integrated with the aerosol foam dispenser. Alternatively, there may be two or more reservoirs.

The reservoir may be comprised of a material selected from the group consisting of rigid materials, flexible materials, and combinations thereof. The reservoir may be comprised of a rigid material if it does not collapse under external atmospheric pressure when it is subject to an interior partial vacuum.

H. Foaming Agent

The hair care composition described herein can comprise a foaming agent. The hair care composition described herein may comprise from about from about 1% to about 10% foaming agent, alternatively from about 2% to about 9% foaming agent, and alternatively from about 3% to about 8% foaming agent, by weight of the hair care composition. The foaming agent can be a propellant. The hair care composition described herein may comprise from about from about 1% to about 10% propellant, alternatively from about 2% to about 9% propellant, and alternatively from about 3% to about 8% propellant, by weight of the hair care composition.

The foaming agent may comprise one or more volatile materials, which in a gaseous state, may carry the other components of the hair care composition in particulate or droplet form. The foaming agent may have a boiling point within the range of from about −45° C. to about 5° C. The foaming agent may be liquefied when packaged in convention aerosol containers under pressure. The rapid boiling of the foaming agent upon leaving the aerosol foam dispenser may aid in the atomization of the other components of the hair care composition.

The foaming agent which may be employed in the hair care compositions described herein may include the chemically-inert hydrocarbons such as propane, n-butane, isobutane, n-pentane, isopentane, and mixtures thereof; chlorofluorocarbons (CFCs) such as dichlorodifluoromethane, 1,1-dichloro-1,1,2,2-tetrafluoroethane, 1-chloro-1,1-difluoro-2,2-trifluoroethane, 1-chloro-1,1-difluoroethylene, monochlorodifluoromethane and mixtures thereof; hydrofluorocarbons (HFCs) such as 1,1-difluoroethane, 1,3,3,3-tetrafluoropropene, 2,3,3,3-tetrafluoropropene and mixtures thereof; hydrofluoroolefins (HFOs) such as 2,3,3,3-tetrafluoropropene (HFO-1234yf), 1,3,3,3-tetrafluoropropene (HFO-1234ze), and mixtures thereof; alkyl ethers such as dimethyl ether, methyl ethyl ether, and mixtures thereof; compressed gases such as carbon dioxide, nitrous oxide, nitrogen, compressed air, and mixtures thereof; and mixtures of one or more hydrocarbons, chlorofluorocarbons, hydrofluorocarbons, hydrofluoroolefins, alkyl ethers, and compressed gases.

The foaming agent may also comprise a blend of hydrocarbons such as isobutane, propane, and butane including, but not limited to, hydrocarbon blend A-46 (15.2% propane, 84.8% isobutane), hydrocarbon blend NP-46 (25.9% propane, 74.1% n-butane), hydrocarbon blend NIP-46 (21.9% propane, 31.3% isobutane, 46.8% n-butane), and other non-limiting hydrocarbon blends designated as A-31, NP-31, NIP-31, A-70, NP-70, NIP-70, A-85, NP-85, A-108. The foaming agent may include chlorofluorocarbons (CFCs) including, but not limited to 1,1-dichloroethane (HFC-152a). The foaming agent may include hydrofluorocarbons (HFCs) including, but not limited to, 1,3,3,3-tetrafluoropropene (HFC-134a). The foaming agent may include hydrofluoroolefins (HFOs) including, but not limited to, 2,3,3,3-tetrafluoropropene (HFO-1234yf), and 1,3,3,3-tetrafluoropropene (HFO-1234ze). The foaming agent may include compressed gases including, but not limited to, carbon dioxide and nitrous oxide.

I. Viscosity

The hair care composition may have a liquid phase viscosity of from about 1 centipoise (cP) to about 40,000 cP, alternatively from about 1,000 to about 30,000 cP, alternatively from about 3,000 cP to about 25,000 cP, alternatively from about 5,000 cP to about 20,000 cP, alternatively from about 7,000 cP to about 15,000 cP, alternatively from about 9,000 cP to about 12,000 cP, alternatively from about 1 cP centipoise to about 3000 cP, alternatively from about 10 cP centipoise to about 3000 cP, alternatively from about 20 cP to about 2000 cP, alternatively from about 500 to about 2000 cP, alternatively from about 750 cP to about 1250 cP, alternatively from about 1000 to about 3000 cP measured at 26.5° C. as defined herein. The viscosities are measured by a Cone and Plate Controlled Stress Brookfield Rheometer R/S Plus, by Brookfield Engineering Laboratories, Stoughton, Mass. The cone used (Spindle C-75-1) has a diameter of 75 mm and 1° angle. The viscosity is determined using a steady state flow experiment at constant shear rate of $2\ s^{-1}$ at a temperature of 26.5° C. The sample size is 2.5 ml and the total measurement reading time is 3 minutes.

J. Perfume

The hair care composition may comprise from about 0.5% to about 7%, alternatively from about 1% to about 6%, and alternatively from about 2% to about 5% perfume, by weight of the hair care composition.

The hair care composition may have a silicone to perfume ratio of from about 95:5 to about 50:50, alternatively from about 90:10 to about 60:40, and alternatively from about 85:15 to about 70:30.

Examples of suitable perfumes may be provided in the CTFA (Cosmetic, Toiletry and Fragrance Association) 1992 international Buyers Guide, published by CFTA Publications and OPD 1993 Chemicals Buyers Directory 80th Annual Edition, published by Schnell Publishing Co. A plurality of perfume components may be present in the hair care composition.

R

K. Optional Ingredients

The hair conditioning composition described herein may optionally comprise one or more additional components known for use in hair care or personal care products, provided that the additional components are physically and chemically compatible with the essential components described herein, or do not otherwise unduly impair product stability, aesthetics or performance. Such optional ingredients are most typically those materials approved for use in cosmetics and that are described in reference books such as the CTFA Cosmetic Ingredient Handbook, Second Edition, The Cosmetic, Toiletries, and Fragrance Association, Inc. 1988, 1992. Individual concentrations of such additional components may range from about 0.001 wt % to about 10 wt % by weight of the conditioning composition.

Emulsifiers suitable as an optional ingredient herein include mono- and di-glycerides, fatty alcohols, polyglycerol esters, propylene glycol esters, sorbitan esters and other emulsifiers known or otherwise commonly used to stabilized air interfaces, as for example those used during preparation of aerated foodstuffs such as cakes and other baked goods and confectionary products, or the stabilization of cosmetics such as hair mousses.

Further non-limiting examples of such optional ingredients include preservatives, perfumes or fragrances, cationic polymers, viscosity modifiers, coloring agents or dyes, conditioning agents, hair bleaching agents, thickeners, moisturizers, foam boosters, additional surfactants or nonionic cosurfactants, emollients, pharmaceutical actives, vitamins or nutrients, sunscreens, deodorants, sensates, plant extracts, nutrients, astringents, cosmetic particles, absorbent particles, adhesive particles, hair fixatives, fibers, reactive agents, skin lightening agents, skin tanning agents, anti-dandruff agents, perfumes, exfoliating agents, acids, bases, humectants, enzymes, suspending agents, pH modifiers, hair colorants, hair perming agents, pigment particles, anti-acne agents, anti-microbial agents, sunscreens, tanning agents, exfoliation particles, hair growth or restorer agents, insect repellents, shaving lotion agents, non-volatile solvents or diluents (water-soluble and water-insoluble), co-solvents or other additional solvents, and similar other materials.

Anti-Dandruff Actives

The hair care compositions described herein may also contain an anti-dandruff agent. Suitable, non-limiting examples of anti-dandruff particulates include: pyridinethione salts, selenium sulfide, particulate sulfur, and mixtures thereof. Such anti-dandruff particulate should be physically and chemically compatible with the essential components of the composition, and should not otherwise unduly impair product stability, aesthetics or performance.

1. Pyridinethione Salts

Pyridinethione anti-dandruff particulates, especially 1-hydroxy-2-pyridinethione salts, can be a particulate anti-dandruff agents for use in compositions of the present invention. The concentration of pyridinethione anti-dandruff particulate typically ranges from about 0.1% to about 10%, by weight of the composition. The concentration of pyridinethione anti-dandruff particulate ranges from about 0.1% to about 8%, and alternatively, ranges from about 0.3% to about 5%. Pyridinethione salts can include those formed from heavy metals such as zinc, copper, tin, cadmium, magnesium, aluminum and zirconium. A pyridinethione salts formed from a heavy metal zinc, and can be the zinc salt of 1-hydroxy-2-pyridinethione (known as "zinc pyridinethione" or "ZPT"), and alternatively 1-hydroxy-2-pyridinethione salts in platelet particle form, wherein the particles have an average size of up to about 20µ. The particles can have an average size up to about 5µ, and alternatively up to about 2.5µ. Salts formed from other cations, such as sodium, may also be suitable. Pyridinethione anti-dandruff agents are described, for example, in U.S. Pat. Nos. 2,809,971; 3,236,733; 3,753,196; 3,761,418; 4,345,080; 4,323,683; 4,379,753; and 4,470,982. It is contemplated that when ZPT is used as the anti-dandruff particulate in the compositions herein, that the growth or re-growth of hair may be stimulated or regulated, or both, or that hair loss may be reduced or inhibited, or that hair may appear thicker or fuller.

2. Other Anti-Microbial Actives

In addition to the anti-dandruff active selected from polyvalent metal salts of pyrithione, the present invention may further comprise one or more anti-fungal or anti-microbial actives in addition to the metal pyrithione salt actives. Suitable anti-microbial actives include coal tar, sulfur, whitfield's ointment, castellani's paint, aluminum chloride, gentian violet, octopirox (piroctone olamine), ciclopirox olamine, undecylenic acid and it's metal salts, potassium permanganate, selenium sulphide, sodium thiosulfate, propylene glycol, oil of bitter orange, urea preparations, griseofulvin, 8-Hydroxyquinoline ciloquinol, thiobendazole, thiocarbamates, haloprogin, polyenes, hydroxypyridone, morpholine, benzylamine, allylamines (such as terbinafine), tea tree oil, clove leaf oil, coriander, palmarosa, berberine, thyme red, cinnamon oil, cinnamic aldehyde, citronellic acid, hinokitol, ichthyol pale, Sensiva SC-50, Elestab HP-100, azelaic acid, lyticase, iodopropynyl butylcarbamate (IPBC), isothiazalinones such as octyl isothiazalinone and azoles, and combinations thereof. Anti-microbials can include itraconazole, ketoconazole, selenium sulphide and coal tar.

a. Azoles

Azole anti-microbials include imidazoles such as benzimidazole, benzothiazole, bifonazole, butaconazole nitrate, climbazole, clotrimazole, croconazole, eberconazole, econazole, elubiol, fenticonazole, fluconazole, flutimazole, isoconazole, ketoconazole, lanoconazole, metronidazole, miconazole, neticonazole, omoconazole, oxiconazole nitrate, sertaconazole, sulconazole nitrate, tioconazole, thiazole, and triazoles such as terconazole and itraconazole, and combinations thereof. When present in the composition, the azole anti-microbial active is included in an amount from about 0.01% to about 5%. The azole anti-microbial active can be included in an amount from about 0.1% to about 3%, and alternatively, from about 0.3% to about 2%, by weight of the composition. The azole anti-microbial can be ketoconazole.

b. Selenium Sulfide

Selenium sulfide is a particulate anti-dandruff agent suitable for use in the anti-microbial compositions of the present invention, effective concentrations of which range from about 0.1% to about 4%, by weight of the composition, and alternatively, from about 0.3% to about 2.5%, and in alternatively from about 0.5% to about 1.5%. Selenium sulfide is generally regarded as a compound having one mole of selenium and two moles of sulfur, although it may also be a cyclic structure that conforms to the general formula $Se_xS_y$, wherein $x+y=8$. Average particle diameters for the selenium sulfide are typically less than 15 µm, as measured by forward laser light scattering device (e.g. Malvern 3600 instrument), and alternatively, less than 10 µm. Selenium sulfide compounds are described, for example, in U.S. Pat. Nos. 2,694,668; 3,152,046; 4,089,945; and 4,885,107.

c. Sulfur

Sulfur may also be used as a particulate anti-microbial/anti-dandruff agent in the anti-microbial compositions of the present invention. Effective concentrations of the particulate sulfur are typically from about 1% to about 4%, by weight of the composition, and alternatively from about 2% to about 4%.

d. Keratolytic Agents

The present invention may further comprise one or more keratolytic agents such as Salicylic Acid.

e. Additional Anti-Microbial Actives

Additional anti-microbial actives of the present invention may include extracts of *melaleuca* (tea tree) and charcoal. The present invention may also comprise combinations of anti-microbial actives. Such combinations may include octopirox and zinc pyrithione combinations, pine tar and sulfur combinations, salicylic acid and zinc pyrithione combinations, octopirox and climbasole combinations, and salicylic acid and octopirox combinations, zinc pyrithione and climbasole and mixtures thereof. These actives, when used herein, are used at levels of from about 1% to about 4%, and alternatively, from about 2% to about 4%.

The composition comprises an effective amount of a zinc-containing layered material. The composition can comprise from about 0.001% to about 10%, or from about 0.01% to about 7%, or from about 0.1% to about 5% of a zinc-containing layered material, by total weight of the composition.

Zinc-containing layered materials may be those with crystal growth primarily occurring in two dimensions. It is conventional to describe layer structures as not only those in which all the atoms are incorporated in well-defined layers, but also those in which there are ions or molecules between the layers, called gallery ions (A. F. Wells "Structural Inorganic Chemistry" Clarendon Press, 1975). Zinc-containing layered materials (ZLMs) may have zinc incorporated in the layers and/or be components of the gallery ions. The following classes of ZLMs represent relatively common examples of the general category and are not intended to be limiting as to the broader scope of materials which fit this definition.

Many ZLMs occur naturally as minerals. The ZLM can be selected from the group consisting of: hydrozincite (zinc carbonate hydroxide), basic zinc carbonate, aurichalcite (zinc copper carbonate hydroxide), rosasite (copper zinc carbonate hydroxide), and mixtures thereof. Related minerals that are zinc-containing may also be included in the composition. Natural ZLMs can also occur wherein anionic layer species such as clay-type minerals (e.g., phyllosilicates) contain ion-exchanged zinc gallery ions. All of these natural materials can also be obtained synthetically or formed in situ in a composition or during a production process.

Another common class of ZLMs, which are often, but not always, synthetic, is layered double hydroxides. The ZLM can be a layered double hydroxide conforming to the formula $[M^{2+}_{1-x}M^{3+}_x(OH)_2]^{x+}A^{m-}_{x/m} \cdot nH_2O$ wherein some or all of the divalent ions ($M^{2+}$) are zinc ions (Crepaldi, E L, Pava, P C, Tronto, J, Valim, J B *J. Colloid Interfac. Sci.* 2002, 248, 429-42).

Yet another class of ZLMs can be prepared called hydroxy double salts (Morioka, H., Tagaya, H., Karasu, M, Kadokawa, J, Chiba, K *Inorg. Chem.* 1999, 38, 4211-6). The ZLM can be a hydroxy double salt conforming to the formula $[M^{2+}_{1-x}M^{2+}_{1+x}(OH)_{3(1-y)}]^+A^{n-}_{(1=3y)/n}\cdot nH_2O$ where the two metal ions ($M^{2+}$) may be the same or different. If they are the same and represented by zinc, the formula simplifies to $[Zn_{1+x}(OH)_2]^{2x+}2x\ A^-\cdot nH_2O$. This latter formula represents (where $x=0.4$) materials such as zinc hydroxychloride and zinc hydroxynitrate. The ZLM can be zinc hydroxychloride and/or zinc hydroxynitrate. These are related to hydrozincite as well wherein a divalent anion replace the monovalent anion. These materials can also be formed in situ in a composition or in or during a production process.

The composition can comprise basic zinc carbonate. Commercially available sources of basic zinc carbonate include Zinc Carbonate Basic (Cater Chemicals: Bensenville, Ill., USA), Zinc Carbonate (Shepherd Chemicals: Norwood, Ohio, USA), Zinc Carbonate (CPS Union Corp.: New York, N.Y., USA), Zinc Carbonate (Elementis Pigments: Durham, UK), and Zinc Carbonate AC (Bruggemann Chemical: Newtown Square, Pa., USA). Basic zinc carbonate, which also may be referred to commercially as "Zinc Carbonate" or "Zinc Carbonate Basic" or "Zinc Hydroxy Carbonate", is a synthetic version consisting of materials similar to naturally occurring hydrozincite. The idealized stoichiometry is represented by $Zn_5(OH)_6(CO_3)_2$ but the actual stoichiometric ratios can vary slightly and other impurities may be incorporated in the crystal lattice.

In embodiments having a zinc-containing layered material and a pyrithione or polyvalent metal salt of pyrithione, the ratio of zinc-containing layered material to pyrithione or a polyvalent metal salt of pyrithione can be from about 5:100 to about 10:1, or from about 2:10 to about 5:1, or from about 1:2 to about 3:1.

Method of Treating Hair

The method of treating the hair described herein can comprise (1) providing a hair care composition, as described herein, (2) dispensing the hair care composition as a liquid form or a foam form using a mechanical foam dispenser or an aerosol foam dispenser; (3) applying the composition to the hair; and (4) rinsing the composition from the hair. The hair care composition can form a stable dosage of foam. A dosage of foam is stable when it substantially sustains its volume from the time of dispensing to its application onto the hair.

The container can be filled with the hair care composition using a standard process known in the art. The container can be shaken to homogenize the composition prior to dispensing. For example, the container can be shaken between 1 to 10 times either immediately before dispensing or up to 24 hr before dispensing.

Aerosol Foam Dispenser

The hair care compositions described herein can be dispensed via and aerosol foam dispenser. The aerosol foam dispenser may comprise a reservoir for holding the concentrated hair treatment composition. The reservoir may be made out of any suitable material selected from the group consisting of plastic, metal, alloy, laminate, and combinations thereof. Alternatively, the reservoir may be for onetime use. Alternatively, the reservoir may be removable from the aerosol foam dispenser. Alternatively, the reservoir may be integrated with the aerosol foam dispenser. Alternatively, there may be two or more reservoirs.

The reservoir may be comprised of a material selected from the group consisting of rigid materials, flexible materials, and combinations thereof. The reservoir may be comprised of a rigid material if it does not collapse under external atmospheric pressure when it is subject to an interior partial vacuum.

The aerosol foam dispenser may comprise a dip-tube to enable upright dispensing.

The aerosol foam dispenser may be of the bag on valve type wherein the container comprises an inner bag and an outer container, which encloses the inner bag, while the inner bag has a valve mechanism attached which is movable between an open position and a closed position. The outer container may be formed from metal or plastic or the like, and any of the foaming agents described herein can be filled in a space between the outer container and the inner bag (in this case the foaming agents would be known as propellants to one skilled in the art). The inner bag may be flexible, and can be made from a single material or from a composite material including plastic, which may comprise at least a polymeric layer and a layer which acts as a gas barrier, e.g., made from metal, such as Aluminum. The inner material of the bag may be inert to the contents of the composition, and the inner material may also be impenetrable by the contents of the composition in the bag. The inner bag may comprise a layer of a material which is essentially impermeable to the propellant inside of the bag. The inner bag may comprise a layer of a material which is essentially impermeable to the propellant outside of the bag which generally is not intended to be mixed with the composition in the inner bag during storage.

The foam can have a dosage weight of from about 1 g to about 5 g when dispensed from the aerosol foam dispenser. The foam can also have a dosage weight of from about 1 g to about 7 g when dispensed from the aerosol foam dispenser, alternatively from about 2 g to about 6 g, alternatively from about 2.5 g to about 5 g, and alternatively from about 3 g to about 4.5 g. The dosage may be obtained via a single squeeze or actuation of the aerosol foam dispenser, but may be accomplished via two or more squeezes or actuations of the aerosol foam dispenser.

The hair care compositions as exemplified herein can be delivered as foams using the following aerosol package: an aluminum can with height of 190 mm and diameter of 53 mm with overflow capacity of 330 mL, supplied by CCL container equipped with (a) a Cozy-Foam one-piece actuator, supplied by Lindal; the actuator can be designed to fit a male stem and can include a nozzle channel, wherein the nozzle channel ends in a section with an inner diameter of 0.80 mm having a direction of 125° in relation to the long axis of the container leading to a nozzle having a diameter of 5.8 mm; (b) a valve with a 0.080 inches valve housing orifice and 2×0.040 inch stem orifice, supplied by Aptar; and (c) a dip tube having an inner diameter of 0.025 inches and a length of 190 mm.

Examples & Data

The following examples and data illustrate the formulations and dosages of foam described herein. The exemplified compositions may be prepared by conventional formulation and mixing techniques. It will be appreciated that other modifications of the formulations and dosages of foam described herein within the skill of those in the shampoo formulation art can be undertaken without departing from the spirit and scope of the formulations and dosages of foam described herein. All parts, percentages, and ratios herein are by weight unless otherwise specified. Some components may come from suppliers as dilute solutions. The amount stated reflects the weight percent of the active material, unless otherwise specified.

Data

Consumer Test Methodology

Approximately 40 consumers per product were asked to evaluate a total of four foam products in a sequential monadic incomplete block test. Products were evaluated based on their appearance and spreading properties. Consumers were provided 3.0 g (+/−0.2 g) of product to observe on hand and spread onto a portion of their hair. Self-administered surveys were completed after each product evaluation. Via these surveys consumers provided an assessment of how well the product "Looked like Conditioner" based on a ten point (1-10) dipolar scale (Looks Like—Does not Look Like Conditioner). At analysis stage this scale was reversed to consistently show more of the benefit on the higher end of the scale. All consumer data was reported as an average and tested for significance. Given the sequential monadic incomplete block test design averages are calculated as adjusted means using a mixed model in SAS with random panelists and fixed product and order. The p-values for the multiple comparisons are based on the student t-test and significance was reported for p-values lower than 0.05.

TABLE 1

Test Results

|  | Ex. 1 | Ex. 2 | Ex. 3 | Ex. 4 | Ex. 5 | Ex. 6 | Ex. 7 | Ex. 8 | Ex. 9* |
|---|---|---|---|---|---|---|---|---|---|
| Base Size | 39 | 39 | 45 | 39 | 45 | 38 | 38 | 36 | 38 |
| Looks like Conditioner[1] (1-10) | 5.07 | 5.37 | 7.43 ABFG HI | 6.66 ABG HI | 7.16 ABFG HI | 5.97 H | 5.6 | 4.79 | 5.34 |
| Yield Point (Pa) | 85.77 | 100 | 39.81 | 73.56 | 100 | 39.81 | 73.56 | 18.5 | 15.9 |
| Bubble Size (μm) | 36 | 35 | 27 | 29 | 39 | 31 | 33 | 30 | 48 |
| Density (g/cm$^3$) | 0.0767 | 0.2279 | 0.2543 | 0.1754 | 0.3107 | 0.1436 | 0.07 | 0.06 | 0.144 |

|  | Ex. 10* | Ex. 11 | Ex. 12 | Ex. 13 | Ex. 14 | Ex. 15 | Ex. 16 |
|---|---|---|---|---|---|---|---|
| Looks like Conditioner[1] (1-10) | 5.05 | 4.44 | 5.56 | 4.39 | 4.37 | 4.99 | 3.84 |
| Density (g/cm$^3$) | 0.12 | 0.14 | 0.085 | 0.052 | 0.056 | 0.098 | 0.039 |
| Bubble Size (μm) | 35 | 31 | 49 | 33 | 23 | 32 | 110 |
| Yield Point (Pa) | 10.5 | 10.53 | 31.72 | 47.46 | 48.32 | 25.12 | 8.08 |

|  | Ex. 17 | Ex. 18 | Ex. 19 | Ex. 20 | Ex. 21 | Ex. 22 |
|---|---|---|---|---|---|---|
| Looks like Conditioner[1] (1-10) | 5.51 | 5.98 | 3.89 | 4.65 | 4.52 | 4.77 |
| Density (g/cm$^3$) | 0.138 | 0.134 | 0.043 | 0.125 | 0.016 | 0.240 |
| Bubble Size (μm) | 43 | 39 | 92 | 25 | 39 | 21 |
| Yield Point (Pa) | 50.82 | 29.08 | 18.6 | 37.78 | 63.54 | 41.76 |

[1]Rated on ability to provide improved hair conditioning benefits based on visual examination of foam.
*Examples 9 and 10 are the same formulation. The tests were run on different days with different panelists.

TABLE 2

Tested Compositions

|  | Ex. 1 | Ex. 2 | Ex. 3 | Ex. 4 | Ex. 5 | Ex. 6 | Ex. 7 | Ex. 8 | Ex. 9/10 |
|---|---|---|---|---|---|---|---|---|---|
| Sodium Laureth Sulfate (SLE1S) (1) | 22 | 22 | 22 | 22 | 22 | 22 | 22 | 16 | 0 |
| Sodium Undecyl Sulfate (2) | 0 | 0 | 0 | 0 | 0 | 0 | 0 | 8 | 24 |
| Sodium Lauryl Sulfate (SLS) (3) | 0 | 0 | 0 | 0 | 0 | 0 | 2.25 | 0 | 0 |
| Lauramidopropyl Betaine (4) | 0 | 0 | 0 | 0 | 0 | 0 | 0 | 0 | 6 |
| Dipropylene Glycol (5) | 0 | 0 | 0 | 0 | 0 | 0 | 0 | 0 | 4 |
| Glycerin (6) | 0 | 0 | 0 | 0 | 0 | 0 | 0 | 0 | 0 |
| Linoleamidopropyl PG-Dimonium Chloride Phosphate (7) | 0 | 0 | 0 | 0 | 0 | 0 | 0 | 0.5 | 0 |
| Cocamidopropyl Betaine (8) | 2 | 2 | 2 | 1 | 0 | 0 | 2 | 0 | 0 |
| Glycol Distearate (9) | 0 | 0 | 3 | 3 | 0 | 3 | 0 | 0 | 0 |
| Trihydroxystearin (10) | 0 | 0 | 0 | 0 | 0 | 0 | 0.1 | 0 | 0 |
| Octopirox (11) | 0 | 0 | 0 | 0 | 0 | 0 | 0 | 2 | 0 |

TABLE 2-continued

Tested Compositions

|  |  |  |  |  |  |  |  |  |  |
|---|---|---|---|---|---|---|---|---|---|
| Zinc Pyrithione (12) | 4 | 4 | 4 | 4 | 4 | 4 | 4 | 0 | 0 |
| Zinc Carbonate (13) | 1.61 | 1.61 | 1.61 | 1.61 | 1.61 | 1.61 | 1.61 | 0 | 0 |
| Fragrance (14) | 1.7 | 1.7 | 1.7 | 1.7 | 1.7 | 1.7 | 1.7 | 3 | 2.4 |
| Guar Hydroxypropyltrimonium Chloride (N-Hance 3196) (15) | 0 | 0 | 0 | 0 | 0 | 0 | 0 | 0.4 | 0 |
| Guar Hyrdroxypropyltrimonium Chloride (LMW) (16) | 0.6 | 0.4 | 0.6 | 0.4 | 0.6 | 0.6 | 0.4 | 0 | 0.4 |
| Dimethicone DM5500 (17) | 1 | 1 | 1 | 1 | 1 | 1 | 1 | 0 | 0 |
| Hydrochloric acid (18) | QS | QS | QS | QS | QS | QS | QS | 0 | 0 |
| Preservative (19) | 0.033 | 0.033 | 0.033 | 0.033 | 0.033 | 0.033 | 0.033 | 0.033 | 0.0033 |
| Sodium Xylene Sulfonate (20) | 0 | 0 | 2.5 | 0 | 0 | 0 | 2.5 | 2.6 | 0 |
| Sodium Chloride (21) | 0 | 0 | 0 | 0 | 0 | 0 | 0 | 0 | 1 |
| Citric Acid (22) | 0 | 0 | 0 | 0 | 0 | 0 | 0 | 0 | 0.4 |
| Sodium Benzoate (23) | 0.15 | 0.15 | 0.15 | 0.15 | 0.15 | 0.15 | 0.15 | 0 | 0 |
| Water and Minors (QS to 100%) (24) | QS | QS | QS | QS | QS | QS | QS | QS | QS |
| Blowing Agent A46 (Isobutane and Propane) (25) | 5 | 3 | 0 | 0 | 0 | 0 | 4 | 3.5 | 0 |
| Blowing Agent HF0 (Trans 1,3,3,3 Tetrafluroprop 1 ene) (26) | 0 | 0 | 3 | 4 | 3 | 5 | 0 | 0 | 5.5 |
| PEG 8 Dimethicone A208 MW855 (27) | 0 | 2.5 | 0 | 0 | 0 | 2.5 | 0 | 0 | 0 |

|  | Ex. 11 | Ex. 12 | Ex. 13 | Ex. 14 | Ex. 15 | Ex. 16 |
|---|---|---|---|---|---|---|
| Sodium Laureth Sulfate (SLE1S) [1] | 0 | 18 | 26 | 0 | 18 | 18 |
| Sodium Undecyl Sulfate [2] | 24 | 0 | 0 | 0 | 0 | 0 |
| Sodium Lauryl Sulfate (SLS) [3] | 0 | 0 | 0 | 7 | 0 | 0 |
| Sodium Laureth Sulfate (SLE3S) [28] | 0 | 0 | 0 | 13 | 0 | 0 |
| Sodium trideceth-2-sulfate ST2S [29] | 0 | 8 | 0 | 0 | 8 | 8 |
| Cocamidopropyl Betaine [8] | 0 | 2 | 0 | 0 | 2 | 2 |
| Lauramidopropyl Betaine [4] | 6 | 0 | 0 | 6 | 0 | 0 |
| Sodium Lauroamphoacetate [30] | 0 | 2 | 0 | 0 | 2 | 2 |
| Dipropylene Glycol [5] | 4 | 4 | 0 | 5 | 4 | 4 |
| Glycerin [6] | 0 | 0 | 0 | 0 | 0 | 0 |
| PEO N-12K [31] | 0 | 0.2 | 0 | 0 | 0 | 0 |
| Acrylates Copolymer Aqua SF-1 [32] | 0 | 0.06 | 0 | 0 | 0 | 0 |
| Octopirox [11] | 1 | 0 | 0 | 0 | 0 | 0 |
| Fragrance | 2.4 | 2.4 | 2.4 | 2 | 2.4 | 2.4 |
| Guar Hyrdroxypropyltrimonium Chloride (Jaguar® C500) [16] | 0.4 | 0 | 0.4 | 0.5 | 0.4 | 0.8 |
| Guar, Hydroxylpropyl Trimonium Chloride (N-Hance CG17) [33] | 0 | 0.2 | 0 | 0 | 0 | 0 |
| Guar, Hydroxylpropyl Trimonium Chloride (N-Hance 3271) [34] | 0 | 0.4 | 0 | 0 | 0 | 0 |
| Polyquaternium-6 [35] | 0 | 0.4 | 0 | 0 | 0 | 0 |
| Polyquaternium-10, KG 30M [36] | 0 | 0 | 0 | 0 | 0 | 0 |
| Silicone Emulsion DC1872 [37] | 0 | 0 | 4 | 0 | 0 | 0 |
| Preservative | 0.0033 | 0.0033 | 0.0033 | 0.0033 | 0.0033 | 0.0033 |
| Sodium Xylene Sulfonate [20] | 0 | 0 | 2.4 | 0 | 0 | 0 |
| Sodium Chloride | 1 | 0 | 1.75 | 0 | 0 | 0 |
| Citric Acid | 0.4 | 0.65 | 0.2 | 1.12 | 0.65 | 0.65 |
| Water and Minors (QS to 100%) | QS | QS | QS | QS | QS | QS |

TABLE 2-continued

Tested Compositions

| | | | | | | |
|---|---|---|---|---|---|---|
| Blowing Agent A46 (Isobutane and Propane) [25] | 0 | 0 | 5 | 5 | 0 | 0 |
| Blowing Agent HF0 (Trans 1,3,3,3 Tetrafluroprop 1 ene) [26] | 5.5 | 7 | 0 | 0 | 7 | 15 |

| | Ex. 17 | Ex. 18 | Ex. 19 | Ex. 20 | Ex. 21 | Ex. 22 |
|---|---|---|---|---|---|---|
| Sodium Laureth Sulfate (SLE1S) [1] | 18 | 18 | 18 | 26 | 11.5 | 11.5 |
| Sodium Undecyl Sulfate [2] | 0 | 0 | 0 | 0 | 0 | 0 |
| Sodium Lauryl Sulfate (SLS) [3] | 0 | 0 | 0 | 0 | 0 | 0 |
| Sodium Laureth Sulfate (SLE3S) [28] | 0 | 0 | 0 | 0 | 0 | 0 |
| Sodium trideceth-2-sulfate ST2S [29] | 8 | 8 | 8 | 0 | 0 | 0 |
| Cocamidopropyl Betaine [8] | 2 | 0 | 0 | 0 | 3.5 | 3.5 |
| Lauramidopropyl Betaine [4] | 0 | 0 | 0 | 0 | 0 | 0 |
| Sodium Lauroamphoacetate [30] | 2 | 0 | 0 | 0 | 0 | 0 |
| Dipropylene Glycol [5] | 0 | 0 | 0 | 0 | 0 | 0 |
| Glycerin [6] | 40 | 50 | 30 | 50 | 50 | 65 |
| PEO N-12K [31] | 0 | 0 | 0 | 0 | 0 | 0 |
| Acrylates Copolymer Aqua SF-1 [32] | 0 | 0 | 0 | 0 | 0 | 0 |
| Octopirox [11] | 0 | 0 | 0 | 0 | 0 | 0 |
| Fragrance | 2.4 | 2.4 | 2.4 | 2.4 | 2.4 | 2.4 |
| Guar Hyrdroxypropyltrimonium Chloride (Jaguar ® C500) [16] | 0.4 | 0.4 | 0.4 | 0.4 | 0.4 | 0 |
| Guar, Hydroxylpropyl Trimonium Chloride (N-Hance CG17) [33] | 0 | 0 | 0 | 0 | 0 | 0 |
| Guar, Hydroxylpropyl Trimonium Chloride (N-Hance 3271) [34] | 0 | 0 | 0 | 0 | 0 | 0 |
| Polyquaternium-6 [35] | 0 | 0 | 0 | 0 | 0 | 0 |
| Polyquaternium-10, KG 30M [36] | 0 | 0 | 0 | 0 | 0 | 0.4 |
| Silicone Emulsion DC1872 [37] | 0 | 0 | 0 | 0 | 0 | 0 |
| Preservative | 0.0033 | 0.0033 | 0.0033 | 0.0033 | 0.0033 | 0.0033 |
| Sodium Xylene Sulfonate [20] | 0 | 0 | 0 | 0 | 0 | 0 |
| Sodium Chloride | 0 | 0 | 0 | 0 | 0 | 0 |
| Citric Acid | 0.85 | 0.65 | 0.65 | 0.3 | 0.3 | 0.3 |
| Water and Minors (QS to 100%) | QS | QS | QS | QS | QS | QS |

TABLE 2

Additional Example Compositions

| | Example Number | | | |
|---|---|---|---|---|
| | Ex. A | Ex. B | Ex. C | Ex. D |
| Sodium Laureth Sulfate (SLE1S) (1) | 24 | 26 | 28 | 28 |
| Sodium Undecyl Sulfate (2) | 0 | 0 | 0 | 0 |
| Sodium Lauryl Sulfate (SLS) (3) | 0 | 0 | 0 | 0 |
| Lauramidopropyl Betaine (4) | 0 | 0 | 0 | 0 |
| Dipropylene Glycol (5) | 0 | 0 | 0 | 0 |
| Glycerin (6) | 0 | 0 | 0 | 6 |
| Linoleamidopropyl PG-Dimonium Chloride Phosphate (7) | 0 | 0 | 0 | 0 |
| Cocamidopropyl Betaine (8) | 0 | 0 | 0 | 0 |
| Glycol Distearate (9) | 1.5 | 1.5 | 1.5 | 1.5 |
| Trihydroxystearin (10) | 0 | 0 | 0 | 0 |
| Octopirox (11) | 0 | 0 | 1 | 1 |
| Zinc Pyrithione (12) | 1.5 | 1.5 | 1.5 | 4 |
| Zinc Carbonate (13) | 1.61 | 1.61 | 1.61 | 1.61 |
| Fragrance (14) | 1.7 | 1.7 | 1.7 | 1.7 |
| Guar Hydroxypropyltrimonium Chloride (N-Hance 3196) (15) | 0 | 0 | 0 | 0 |
| Guar Hyrdroxypropyltrimonium Chloride (LMW) (16) | 0.4 | 0.4 | 0.4 | 0.66 |
| Dimethicone DM5500 (17) | 2 | 4 | 6 | 1 |
| Hydrochloric acid (18) | QS | QS | QS | QS |
| Preservative (19) | 0.0033 | 0.0033 | 0.0033 | 0.0033 |
| Sodium Xylene Sulfonate (20) | 2.5 | 3 | 3 | 2.5 |
| Sodium Chloride (21) | 0 | 0 | 0 | 0 |
| Citric Acid (22) | 0 | 0 | 0 | 0 |
| Sodium Benzoate (23) | 0.15 | 0.15 | 0.15 | 0.15 |
| Water and Minors (QS to 100%) (24) | QS | QS | QS | QS |
| Blowing Agent A46 (Isobutane and Propane) (25) | 4.5 | 0 | 0 | 0 |
| Blowing Agent HF0 (Trans 1,3,3,3 Tetrafluroprop 1 ene) (26) | 0 | 5.5 | 5.5 | 5.5 |

TABLE 2-continued

Tested Compositions

| | | | | | | |
|---|---|---|---|---|---|---|
| Blowing Agent A46 (Isobutane and Propane) [25] | 0 | 3 | 0 | 7 | 15 | 0 |
| Blowing Agent HF0 (Trans 1,3,3,3 Tetrafluroprop 1 ene) [26] | 7 | 0 | 15 | 0 | 0 | 5 |

1. Sodium Laureth-1 Sulfate from the Stepan Company
2. Sodium Undecyl Sulfate (C11, Isachem 123S) at 70% active, supplier: P&G
3. Sodium Lauryl Sulfate from Stepan Company
4. LAPB (Mackam DAB), at 35% active level, supplier: Rhodia
5. Dipropylene Glycol from Dow Chemical
6. Glycerin from P&G Chemicals
7. Linoleamidopropyl PG-Dimonium Chloride Phosphate
8. Amphosol HCA from Stepan Company
9. Glycol Distearate from Golschmidt Chemical Company
10. Trihydroxystearin Elementis Specialties
11. Octopirox from Clariant
12. U2 ZPT from Lonza
13. Zinc Carbonate from Bruggeman Group
14. Fragrance from P&G Chemicals
15. NHance ™ 3196 from Ashland with a MW of 1,700,000 g/mol and charge density of 0.7 meq/g
16. Jaguar ® C500 from Solvay with a M. Wt of 500,000 g/mol and charge density of 0.8 meq/g
17. Dimethicone DM5500, Wacker Silicone
18. Hydrochloric acid from Mallinckrodt Baker Inc.
19. Preservative Kathon CG from Akzo Nobel
20. Sodium Xylene Sulfonate from Stepan Company
21. Sodium Chloride USP (food grade) Supplier Morton
22. Citric Acid from Cargill Inc.
23. Sodium Benzoate from Kalama Chemical
24. Water from Misty Mountain Spring Water
25. Blowing Agent A46 (Isobutane and Propane) Diversified Cpc International (Channahon US)
26. Blowing Agent HF0 (Trans 1,3,3,3 Tetrafluroprop-1-ene) from Honey Well
27. PEG 8 Dimethicone A208 MW855, Siltech LLC
28. Sodium Laureth-3 Sulfate from the Stepan Company
29. Sodium Tridecyl Ether Sulfate (2 molar ethylene oxide), Stepan ST2S-65 (Steol-TD 402 65) 65% active, supplier: Stepan Co
30. NaLaa (Miranol Ultra L32) at 32% active level, supplier: Solvay
31. Polyox WSR N-12K, polyethylene oxide, MW of 1,000,000, from Dow ®
32. Carbopol ® Aqua SF-1 polymer, acrylates copolymer, from Lubrizol Co.
33. N-Hance ™ CG17, MW of 1,600,000, CD of 1.0, from Ashland
34. N-Hance ™ 3271, MW of 500,000, CD of 0.7, from Ashland
35. Polyquaternium 6, PolyDADMAC, MW of 150,000, CD of 6.2, trade name: Mirapol ® 100s, 31.5% active, from Solvay
36. Ucare Polymer KG-30M, Polyquaternium 10, MW of 1,250,000, CD of 1.9, from Dow ®
37. DC 1872 silicone emulsion (dimethiconol) with an average particle size of 30 nm, from Dow Corning TABLE 2-continued Additional Example Compositions

| | Example Number | | | |
|---|---|---|---|---|
| | Ex. A | Ex. B | Ex. C | Ex. D |
| PEG 8 Dimethicone A208 MW855 (27) | 0 | 0 | 0 | 0 |

(1). Sodium Laureth-1 Sulfate from the Stepan Company
(2). Sodium Undecyl Sulfate (C11, Isachem 123S) at 70% active, supplier: P&G
(3). Sodium Lauryl Sulfate from Stepan Company
(4). LAPB (Mackam DAB), at 35% active level, supplier: Rhodia
(5). Dipropylene Glycol from Dow Chemical
(6). Glycerin from P&G Chemicals
(7). Linoleamidopropyl PG-Dimonium Chloride Phosphate
(8). Amphosol HCA from Stepan Company
(9). Glycol Distearate from Golschmidt Chemical Company
(10). Trihydroxystearin Elementis Specialties
(11). Octopirox from Clariant
(12). U2 ZPT from Lonza
(13). Zinc Carbonate from Bruggeman Group
(14). Fragrance from P&G Chemicals
(15). NHance ™ 3196 from Ashland with a MW of 1,700,000 g/mol and charge density of 0.7 meq/g
(16). Jaguar C500 from Solvay with a M. Wt of 500,000 g/mol and charge density of 0.8 meq/g
(17). Dimethicone DM5500, Wacker Silicone
(18). Hydrochloric acid from Mallinckrodt Baker Inc.
(19). Preservative Kathon CG from Akzo Nobel
(20). Sodium Xylene Sulfonate from Stepan Company
(21). Sodium Chloride USP (food grade) Supplier Morton
(22). Citric Acid from Cargill Inc.
(23). Sodium Benzoate from Kalama Chemical
(24). Water from Misty Mountain Spring Water
(25). Blowing Agent A46 (Isobutane and Propane) Diversified Cpc International (Channahon US)
(26). Blowing Agent HF0 (Trans 1,3,3,3 Tetrafluroprop-1-ene) from Honey Well
(27). PEG 8 Dimethicone A208 MW855, Siltech LLC Test Methods Foam Density & Foam Volume Foam density is measured by placing a 100 ml beaker onto a mass balance, tarring the mass of the beaker and then dispensing product from the aerosol container into the 100 ml beaker until the volume of the foam is above the rim of the vessel. The foam is made level with the top of the beaker by scraping a spatula across it within 10 seconds of dispensing the foam above the rim of the vessel. The resulting mass of the 100 ml of foam is then divided by the volume (100) to determine the foam density in units of g/ml.

Foam volume is measured by placing a weigh boat onto a mass balance, tarring the mass of the weigh boat and then dispensing the desired amount of product from the aerosol container.

The grams of foam dispensed is determined and then divided by the density of foam as determined from the Foam Density methodology to reach a volume of foam in ml or cm3.

Viscosity Cone/Plate Viscosity Measurement

The viscosities of formulations are measured by a Cone/Plate Controlled Stress Brookfield Rheometer R/S Plus, by Brookfield Engineering Laboratories, Stoughton, Mass. The cone used (Spindle C-75-1) has a diameter of 75 mm and 1° angle. The viscosity is determined using a steady state flow experiment at constant shear rate of 2 s$^{-1}$ and at temperature of 26.5° C. The sample size is 2.5 ml and the total measurement reading time is 3 minutes.

Foam Rheology Method (Yield Point)

Foam shampoo is applied to the AR1000 rheometer for foam oscillation stress sweep. 60 mm smooth acrylic plate is utilized for shear stress measurement. Measurement is made at 25 C. The plate head is lowered to 1200 microns and excess foam is removed with a spatula so that drag does not occur during measurement. The measurement gap height is then lowered 1000 microns. Sweep occurs from 0.1 to 400 Pa. Data is analyzed via TA Rheology Advantage Data Analysis software. Yield point is determined at the point at which the oscillatory shear stress begins to deviate from its tangent. The yield point measurements are reported in Pa units.

Kruss Lather Analyzer (Bubble Size)

The commercially available Kruss lather analyzer DFA100, supplied from Kruss, is used to analyze the foam shampoo for the initial Sauter mean radius $R_{32}$ (bubble size). Shampoo foam is dispensed into the CY4571 column containing a prism. An internal stopper is placed into the column approximately 100 ml from the top of the chamber. The camera height is set to 244 mm and camera position is placed in the 3 slot. Structure foaming is captured at 2 frames per second for 120 seconds. Data analysis is performed on the Kruss Advance 1.5.1.0 software application version.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of cleansing and conditioning hair comprising:
   a. providing a shampoo composition comprising:
      i. from about 10 wt. % to about 40 wt. % anionic surfactant; and
      ii. from about 1 wt. % to about 10% propellant;
   b. dispensing the shampoo composition as a dosage of foam using an aerosol foam dispenser wherein the dosage of foam comprises:
      i. a foam density of from about 0.10 g/cm$^3$ to 0.35 g/cm$^3$;
      ii. a bubble size distribution comprising an $R_{32}$ of from about 5 μm to about 90 μm; and
      iii. a yield point of from about 10 Pa to about 100 Pa;
      iv. a gloss unit measurement from about 5 GU and 10 GU;

c. applying the composition to the hair; and
d. rinsing the composition from the hair.

2. The method of claim 1, wherein the bubble size distribution comprises an $R_{32}$ of from about 10 μm to about 60 μm.

3. The method of claim 1, wherein the bubble size distribution comprises an $R_{32}$ of from about 20 μm to about 50 μm.

4. The method of claim 1, wherein the bubble size distribution comprises an $R_{32}$ of from about 25 μm to about 40 μm.

5. The method of claim 1, wherein the yield point is from about 20 Pa to about 100 Pa.

6. The method of claim 1, wherein the yield point is from about 25 Pa to about 100 Pa.

7. The method of claim 1, wherein the yield point is from about 38 Pa to about 100 Pa.

8. The method of claim 1, wherein the volume of the foam is from about 10 cm³ to about 50 cm³.

9. The method of claim 1, wherein the foam density is from about 0.15 g/cm³ to 0.35 g/cm³.

10. The method of claim 1, wherein the foam density is from about 0.20 g/cm³ to 0.35 g/cm³.

11. The method of claim 1, wherein the composition comprises from about 15 wt. % to about 36 wt. % anionic surfactant.

12. The method of claim 11, wherein the composition comprises from about 18 wt. % to about 32 wt. % anionic surfactant.

13. The method of claim 1, wherein the propellant is selected from the group consisting of isobutene, propane, trans 1,3,3,3 tetrafluroprop-1-ene, and mixtures thereof.

14. The method of claim 13, wherein the propellant comprises trans 1,3,3,3 tetrafluroprop-1-ene.

15. The method of claim 1, wherein the composition comprises from about 3 wt. % to about 8 wt. % propellant.

16. The method of claim 1, wherein the composition comprises a liquid phase viscosity of from about 1 cP to about 5000 cP.

17. The method of claim 16, wherein the composition comprises a liquid phase viscosity of from about 1 cP to about 3000 cP.

18. The method of claim 1, wherein the composition further comprises an anti-dandruff agent selected from the group consisting of octopirox, zinc pyrithione, and mixtures thereof.

* * * * *